(12) United States Patent
McGreevy

(10) Patent No.: US 7,317,955 B2
(45) Date of Patent: Jan. 8, 2008

(54) VIRTUAL OPERATING ROOM INTEGRATION

(75) Inventor: Francis T. McGreevy, Aurora, CO (US)

(73) Assignee: ConMed Corporation, Utica, NY (US)

( * ) Notice: Subject to any disclaimer, the term of this patent is extended or adjusted under 35 U.S.C. 154(b) by 472 days.

(21) Appl. No.: 10/735,573

(22) Filed: Dec. 12, 2003

(65) Prior Publication Data

US 2005/0128184 A1    Jun. 16, 2005

(51) Int. Cl.
- *A61B 1/00*   (2006.01)
- *A61B 18/04*  (2006.01)
- *A61B 18/18*  (2006.01)
- *A61N 1/00*   (2006.01)
- *G05B 15/00*  (2006.01)

(52) U.S. Cl. ............... 700/83; 378/8; 378/168; 378/179; 600/101; 600/118; 382/103; 607/115; 607/119; 607/122; 606/34; 606/41; 606/35

(58) Field of Classification Search ............. 700/83; 378/8; 345/168, 179, 8; 600/101, 118, 437; 382/103; 414/7; 351/206; 606/34–50; 607/115–123

See application file for complete search history.

(56) References Cited

U.S. PATENT DOCUMENTS

| | | | |
|---|---|---|---|
| 5,370,645 A * | 12/1994 | Klicek et al. | 606/35 |
| 5,524,180 A * | 6/1996 | Wang et al. | 600/118 |
| 5,599,151 A * | 2/1997 | Daum et al. | 414/7 |
| 5,678,568 A | 10/1997 | Uchikubo et al. | |
| 6,063,030 A * | 5/2000 | Vara et al. | 600/437 |
| 6,175,610 B1 * | 1/2001 | Peter | 378/8 |
| 6,227,667 B1 * | 5/2001 | Halldorsson et al. | 351/206 |
| 6,231,569 B1 * | 5/2001 | Bek et al. | 606/34 |
| 6,286,512 B1 * | 9/2001 | Loeb et al. | 128/898 |
| 6,323,942 B1 | 11/2001 | Bamji | |
| 6,377,238 B1 | 4/2002 | McPheters | |
| 6,402,741 B1 * | 6/2002 | Keppel et al. | 606/34 |
| 6,512,838 B1 | 1/2003 | Rafii et al. | |
| 6,515,740 B2 | 2/2003 | Bamji et al. | |
| 6,522,395 B1 | 2/2003 | Bamji et al. | |
| 6,580,496 B2 | 6/2003 | Bamji et al. | |

(Continued)

FOREIGN PATENT DOCUMENTS

DE         19714984 A1     11/1997

(Continued)

OTHER PUBLICATIONS

International Application Publication No. WO 02/100285 A1; International Application No. PCT/SG01/00119; dated Dec. 19, 2002.

(Continued)

*Primary Examiner*—Anthony Knight
*Assistant Examiner*—Sunray Chang
(74) *Attorney, Agent, or Firm*—John R. Ley

(57) ABSTRACT

A virtual control system for an operating room establishes virtual control devices to control surgical equipment and patient monitoring equipment and to display control, status and functionality information concerning the surgical equipment and condition information of the patient. The virtual control devices permit direct interaction by the surgeon while maintaining a sterile field, and avoid the use of actual physical devices and electrical cables connecting them to the surgical equipment.

112 Claims, 9 Drawing Sheets

U.S. PATENT DOCUMENTS

| | | | |
|---|---|---|---|
| 6,587,186 B2 | 7/2003 | Bamji et al. | |
| 6,603,464 B1 * | 8/2003 | Rabin | 345/179 |
| 6,633,658 B1 * | 10/2003 | Dabney et al. | 382/128 |
| 6,710,770 B2 * | 3/2004 | Tomasi et al. | 345/168 |
| 6,801,637 B2 * | 10/2004 | Voronka et al. | 382/103 |
| 6,847,336 B1 * | 1/2005 | Lemelson et al. | 345/8 |
| 7,052,494 B2 * | 5/2006 | Goble et al. | 606/45 |
| 7,074,179 B2 * | 7/2006 | Wang et al. | 600/101 |
| 7,226,447 B2 * | 6/2007 | Uchida et al. | 606/34 |

FOREIGN PATENT DOCUMENTS

| | | |
|---|---|---|
| DE | 19805529 A1 | 8/1999 |
| DE | 20001134 U1 | 6/2000 |

OTHER PUBLICATIONS

PCT International Search Report for International Application No. PCT/US2004/041337, dated Apr. 12, 2005.

Written Opinion of the International Searching Authority for International Application No. PCT/US2004/041337, dated Apr. 12, 2005.

PCT International Search Report for International Application No. PCT/US2004/041336, dated Apr. 15, 2005.

Written Opinion of the International Searching Authority for International Application No. PCT/US2004/041336, dated Apr. 15, 2005.

Holograp Controls, Keep Operating Rooms Clean and Uncluttered; Medical Design News, May/Jun. 2003; pp. 10 and 12.

Type It Anywhere, Mike May, Scientific American, Jan. 2003, pp. 32 and 33.

* cited by examiner

VIRTUAL OPERATING ROOM INTEGRATION

CROSS-REFERENCE TO RELATED APPLICATION

This invention is related to another invention made by the present inventor for Virtual Control of Electrosurgical Generator Functions described in U.S. patent application Ser. No. (24.355), filed concurrently herewith. The subject matter of this concurrently filed application is incorporated herein by this reference.

FIELD OF THE INVENTION

This invention relates to integrating surgical equipment in one or more operating rooms using virtual control devices and optical displays. More particularly, the present invention relates to a new and improved virtual control system and method which optically senses the position of a surgeon's foot or finger with respect to a projected image of a virtual control device associated with the surgical equipment and which controls the surgical equipment in relation to the sensed position of the foot or finger. The present invention also relates to a new and improved system and method for displaying information describing the condition of a patient at a location within the operating room which is convenient for observation and remote from patient monitoring equipment from which the information was obtained. The virtual control permits the surgeon to control the surgical equipment directly while remaining in a sterile field, and the display of the patient information directly informs the surgeon of the patient's condition, thus contributing to more effective integration of numerous control and information communications functions within the operating room, among other improvements.

BACKGROUND OF THE INVENTION

Electrically operated surgical equipment has various controls to adjust different functions and output characteristics of the equipment. For instance, activating an electrosurgical generator by depressing a foot switch causes electrical energy to be delivered to the tissue. The amount of power delivered and the characteristics of the power delivered are selected and adjusted from front panel controls, to cut the tissue, coagulate blood flow from the tissue, or simultaneously cut and coagulate. Other types of surgical equipment have similar activation and control characteristics as well as similar front panel controls.

The front panel controls of the surgical equipment cannot be positioned within the sterile field where the surgeon is operating because it is not possible to disinfect and sterilize the entire surgical equipment of which the front panel controls are a part. Instead, the surgeon must rely on an assistant to make adjustments to the front panel controls, and that assistant must remain outside of the sterile field. Adjustments to the front panel controls are achieved in response to verbal commands from the surgeon, and such verbal communication may be prone to misinterpretation. In any event, the necessity to rely on an assistant for indirect control over non-sterile surgical equipment can become a distraction to the surgeon, particularly in procedures which require numerous adjustments during the course of the procedure.

Each surgeon typically has preferred settings for the surgical equipment, to give the best results for a particular type of surgical procedure in accordance with the surgeon's particular manner of performing the procedure. The preferred settings must be remembered and established before beginning the procedure. Failing to establish or remember the preferred settings can require additional adjustments to be made during the procedure and is distracting to the progress of the procedure.

Foot switches are located underneath the operating table upon which the patient is placed for the procedure. The foot switches are therefore located outside of the sterile field. However, foot switches are relatively bulky and heavy and are connected to the surgical equipment by a cable that extends along the floor. Foot switches and their cables can clutter the floor of an operating room, particularly when more than one foot switch is used. The foot switches and their cables may pose a tripping hazard that can be especially distracting to the numerous people working and moving about the operating table. Even though they are located outside of the sterile field, foot switches and their cables are a potential source of introducing pathogens into the operating room.

It is not unusual for two different surgeons to use the same surgical equipment in an alternating manner during the course of a procedure. In this situation, the foot switch must be moved between different positions where the two surgeons can reach it. Moving the foot switch back and forth in this manner is difficult due to its bulk and because the cable extending from the foot switch further complicates movement. Moving the foot switch is time consuming, inconvenient and inefficient because of the delay involved in moving and positioning the foot switch. Moreover, an assistant operating outside of the sterile field must be used to position the foot switch. When the foot switch is moved, or when the surgeon shifts his or her position, the surgeon may experience difficulty in locating the position of the foot switch for use, thereby distracting attention from the procedure.

One approach to dealing with some of these problems utilizes a holograph to project an image of the controls for the surgical equipment into empty three-dimensional space within the operating room. When an object enters the three-dimensional space in which the holographic image of the controls is located, an adjustment to the equipment is made. Allowing the surgeon to interact with a holographic image allows the surgeon to establish direct control over the surgical equipment without compromising the sterile field, but holographic images introduce new problems. One such problem stems from the fact that holographic images can only be viewed from a relatively narrow field of vision, which means that they cannot always be seen by the surgeon. For the surgeon to view the holographic controls, the light projection equipment that creates the hologram has to be adjusted in a particular location in the operating room, or the surgeon must shift his or her position at the operating table, or the surgeon must again rely on an assistant to interact with the hologram to achieve control over the surgical equipment. Moreover, because the hologram exists in three-dimensional space, an individual or object can inadvertently move through the three-dimensional space and interact with the hologram in such a way to create an unintended adjustment of or control over the surgical equipment.

The holographic controls for surgical equipment do not effectively deal with the problem of clutter caused by the bulky foot switches and their attached cables beneath the operating table. Holographic controls can not be conveniently located near the floor because of the necessity to focus the holographic image at a location where interaction with it is possible.

Another circumstance which may result in distraction or inconvenience to the surgeon during the procedure relates to informing the surgeon of various physiological and other conditions of the patient during the procedure. It is typical that monitoring equipment is connected to the patient during the surgical procedure to monitor the condition of the patient. Such patient monitoring equipment typically includes integrally connected monitors and displays which present the information describing the condition of the patient. These monitors and displays are large and complex devices and are sometimes integrated with the patient monitoring equipment itself, thereby making it essentially impossible to sterilize this equipment. Consequently, the patient monitoring equipment and associated display devices must therefore remain outside of the sterile field and outside of the direct view and observation of the surgeon while performing the procedure at the surgical site.

The surgeon must rely on an assistant to communicate verbally the relevant patient condition information or to alert the surgeon of the necessity to divert his attention from the surgical site to view a monitor or display located elsewhere within the operating room. Periodically diverting the surgeon's attention away from the surgical site is a distraction and a complication to the surgeon, particularly in very intense and tedious procedures. Relying on an assistant to communicate relevant patient information to the surgeon is subject to miscommunication and misinterpretation.

A similar situation exists with respect to information describing the performance of the surgical equipment. In those circumstances where the surgeon wishes to observe a performance characteristic of the surgical equipment, such as the total amount of electrical energy delivered to the patient during a particular length of time or during an activation time interval of the surgical equipment, the surgeon must divert his attention from the surgical site to view a display or monitor associated with the surgical equipment. The need to continually divert attention from the surgical site is an inconvenience and distraction. In some procedures, the surgeon must focus intently on the procedure at the same time that the surgeon desires to observe and evaluate the performance of the surgical equipment. However, since the surgeon cannot divert his or her attention from the surgical site, it becomes impossible to simultaneously monitor the performance of the surgical equipment while using that surgical equipment.

SUMMARY OF THE INVENTION

The present invention involves a system and method for controlling and using equipment in an operating room through the use of virtual control devices. The virtual control devices project images on surfaces, and the surgeon interacts with the images to control the equipment, such as surgical equipment and patient monitoring equipment. The images created by the virtual control devices may include a front control panel to control the equipment and a foot switch to activate and deactivate the surgical equipment. The images from the virtual control devices may be displayed and presented at locations which are within the sterile field so that the surgeon may interact with them directly rather than rely on surgical personnel to achieve control and adjustment of the equipment. More direct and accurate control over the surgical instrument is obtained. Traditional foot switches with cables are eliminated, thereby eliminating the clutter and risk of tripping created by such equipment as well as a source of pathogens within the operating room. The virtual control devices can be positioned for the most expeditious use, and the images from the virtual control devices can be moved from one location to another by changing the location of the light projection which creates the images.

The present invention also involves a system and method for displaying information obtained from patient monitoring equipment and the surgical equipment in an expeditious, convenient and non-distracting manner for use by the surgeon during the surgical procedure. Display images are projected in a manner which does not require the surgeon to substantially divert his attention from the surgical site, such as by presenting the information in a heads up display projected onto a face shield worn by the surgeon. In addition or alternatively, the display images are projected in a manner which minimizes the amount of diversion of attention required from the surgeon, and in a manner which makes the display images conveniently observable to the operating room personnel. The information displayed may include the control, status and functionality information of the surgical equipment and vital statistics and signs indicating the condition of the patient. The images presenting the information may be displayed and presented at locations within the sterile field so that the surgeon may observe the information directly while performing the procedure rather than rely on surgical personnel to communicate that information. More immediate and accurate communication of information is obtained. The information displays can be positioned for the most expeditious use, and the images can be moved from one location to another by changing the location of the light projection which creates the images.

Preferred settings for using the surgical equipment are established in response to scanning or reading information which identifies the particular procedure or surgeon performing the procedure. Unauthorized and accidental activations and adjustments to the surgical equipment may be prevented and avoided. Certainty concerning the identity of the patient and the type of surgical procedure to be performed are also obtained by reading information made available for use by the system.

The communication links to establish this functionality are preferably wireless, to eliminate the clutter and risks of tripping over further physical objects within the operating room and to facilitate advantageous positioning of the virtual control devices. The functionality of the present invention is available to be used with a variety of different types of surgical equipment made by different manufacturers, even though that surgical equipment was not originally intended to be used in the manner contemplated by the present invention.

These and other features of the invention are achieved by a virtual control system for controlling surgical equipment in an operating room while a surgeon performs a surgical procedure on a patient. The virtual control system comprises a virtual control device including an image of a control device and a sensor for interrogating interaction of an object with the image. An interaction signal indicative of the interaction of the object with the image is delivered to a system controller. The system controller responds to the interaction signal from the virtual control device and delivers a control signal to the surgical equipment. The control signal controls the surgical equipment in response to the interaction of the object with the image.

A related aspect of the invention is achieved by a method for controlling surgical equipment in an operating room while a surgeon performs a surgical procedure on a patient. The method comprises creating an image of a control device for the surgical equipment, interrogating the interaction of a part of the surgeon, such as a finger or foot, with the image and controlling the surgical equipment in response to the interaction of the object with the image.

Other aspects of the invention involve a system and method for use with surgical equipment and/or patient monitoring equipment in an operating room while a surgeon performs a surgical procedure on a patient. The system comprises a system controller connected to the surgical equipment to obtain information from the surgical equipment concerning the status, control and functionality of the surgical equipment, and/or to obtain information describing the condition of the patient from the patient monitoring equipment. A projector connected to the system controller creates a display image at a location within the operating room removed from the surgical equipment. The display image displays the information describing the control, status and functionality of the surgical equipment, and/or the information describing the condition of the patient.

Preferable aspects of the invention involve projecting images of a front control panel and a foot switch, and interrogating the interaction of a surgeon's finger or foot with these projected images to control the surgical equipment and/or the display of information; displaying information on a face shield worn by the surgeon; interrogating the position of a position tag worn on the foot of the surgeon relative to a projected image of the foot switch; indicating the proximity of the surgeon's foot relative to the projected image of the foot switch; reading information from an identification tag associated with at least one of either the surgeon or the patient which identifies the surgeon, the patient or the surgical procedure, and responding to the information read from the identification tag to control the surgical equipment and/or the display of information; among others.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

DETAILED DESCRIPTION

Figure 1:
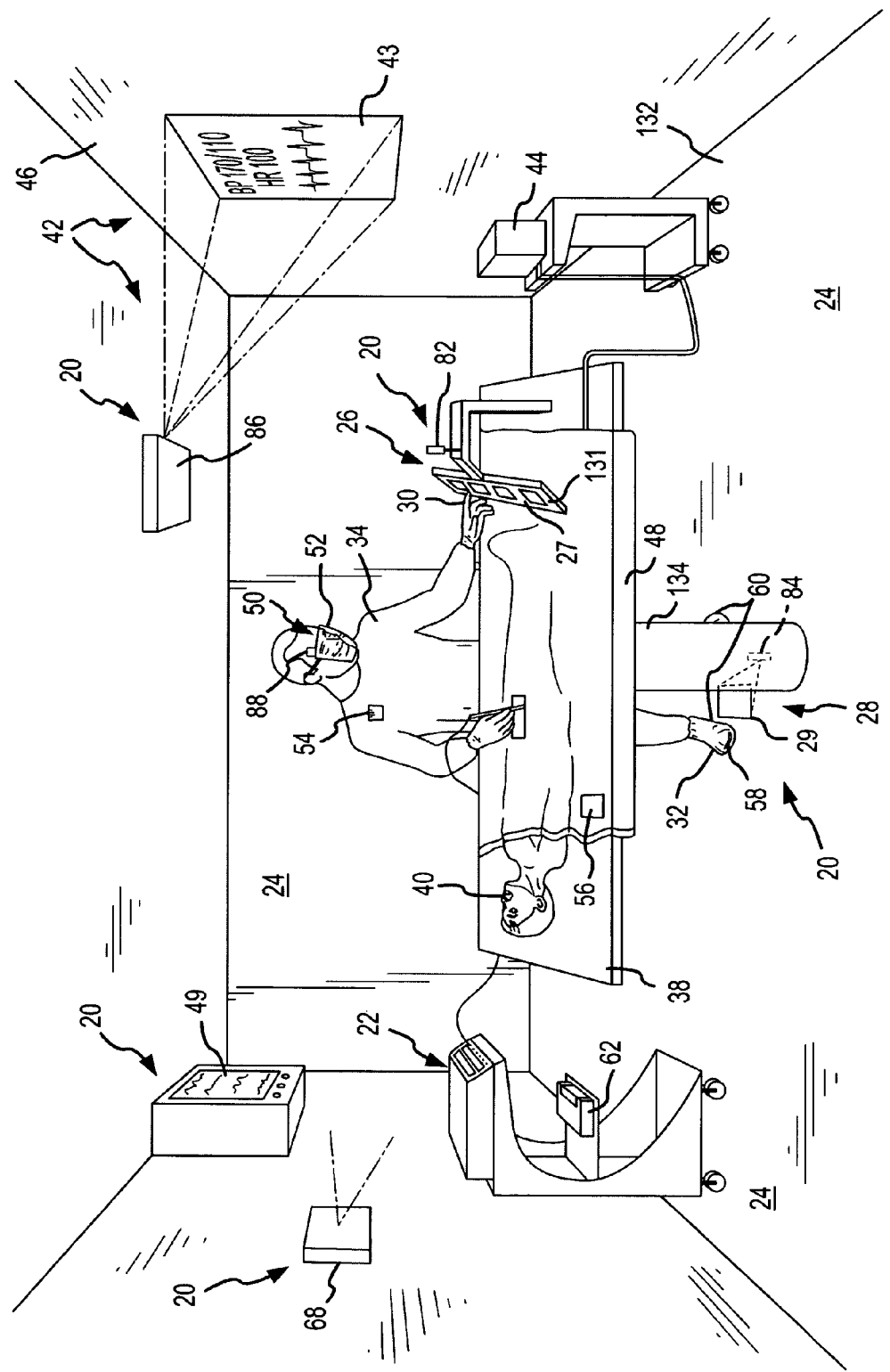
FIG. 1 is a perspective view of an operating room which shows a virtual integration or control and display system in which the present invention is embodied.
Figure 2:
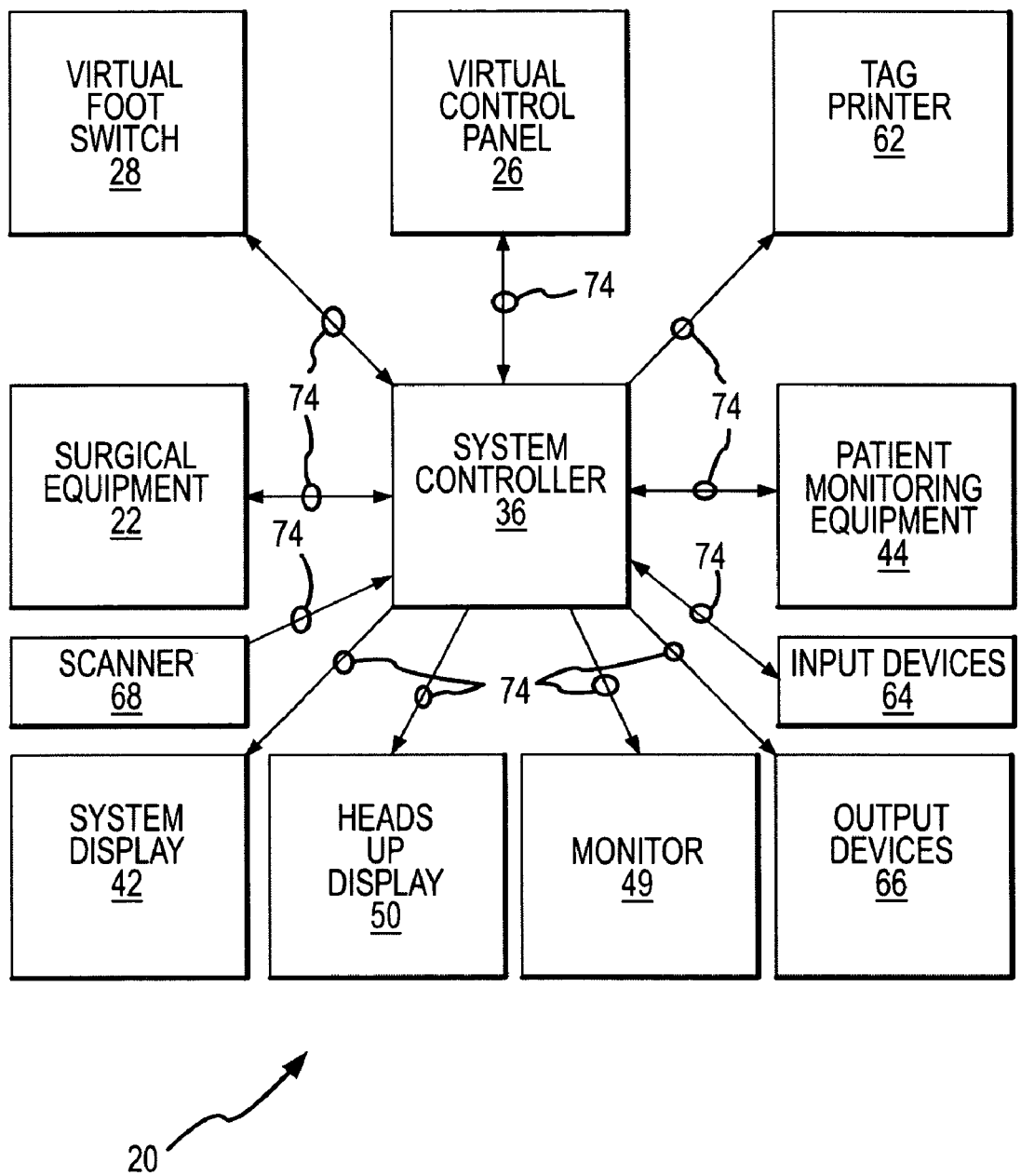
FIG. 2 is an illustration of virtual and functional components and their communication relationships in the system shown in FIG. 1.
Figure 3:
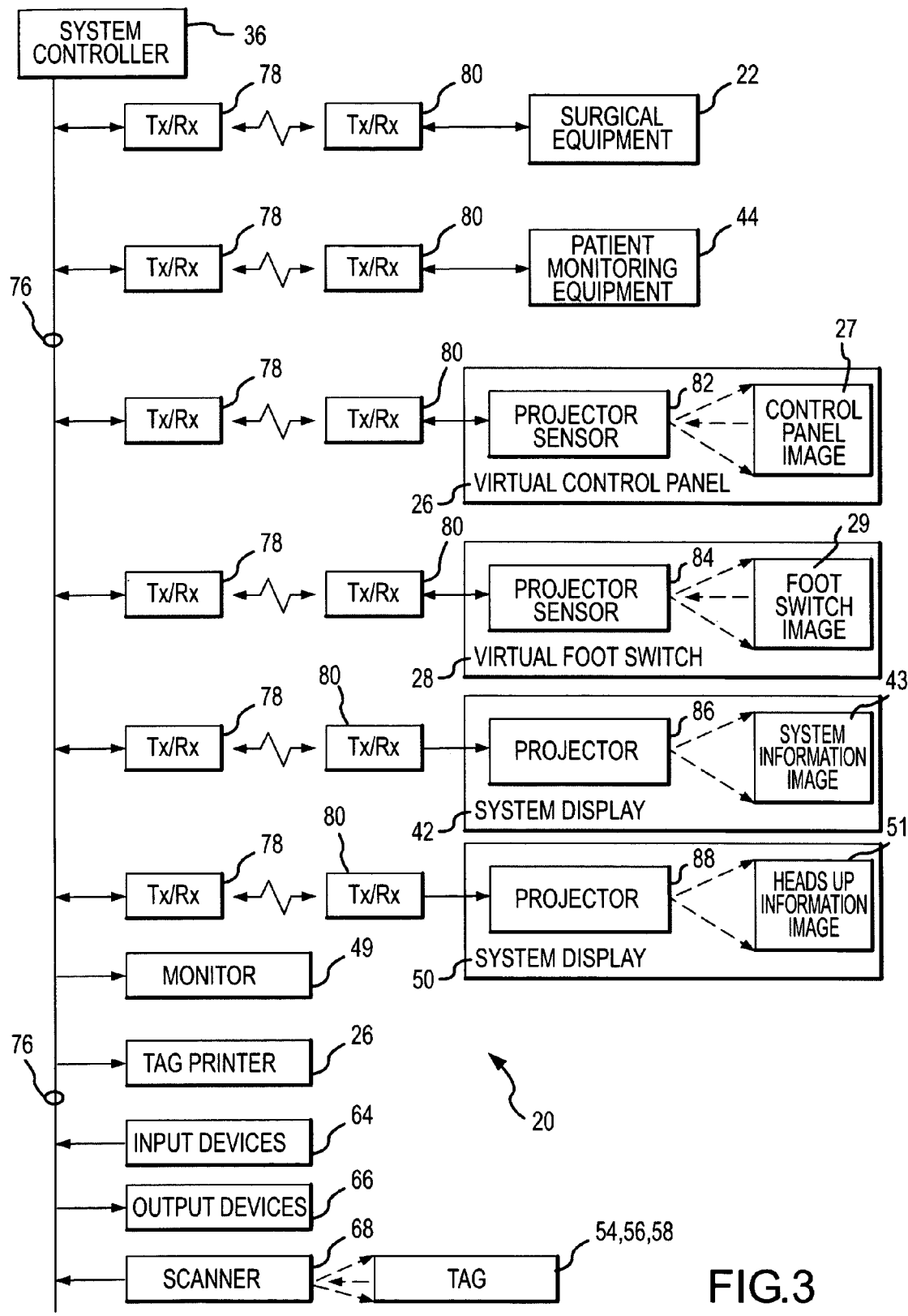
FIG. 3 is a functional block diagram of the components of the system shown in FIGS. 1 and 2.

An exemplary form of the present invention is embodied in a virtual integration or control system 20 for controlling surgical equipment 22, among other things, in an operating room 24, as shown in FIGS. 1-3. The virtual control system includes a virtual control panel 26 and a virtual foot switch 28 created by projecting an image 27 of a control panel and an image 29 of a foot switch. Physical interaction of a finger 30 or foot 32 of the surgeon 34 with the control panel image 27 and the foot switch image 29, respectively, is then interrogated and interpreted as a control input to the surgical equipment. A system controller 36 (FIGS. 2 and 3) of the virtual control system 20 controls the surgical equipment 22 in response to that interrogation and interaction. For example, direct physical interaction of the surgeon's finger 30 with the projected control panel image 27 may result in adjusting the output power and output signal characteristics from the surgical equipment 22, and direct physical interaction of the surgeon's foot 32 with the projected foot switch image 29 may activate and deactivate the power delivery from the surgical equipment 22. In essence, the direct physical interaction with the projected images 27 and 29 of the virtual control devices 26 and 28 controls the functionality of the surgical equipment 22 in a manner substantially equivalent to the manner in which the surgical equipment 22 is controlled by direct physical manipulation of a conventional physical control panel (not shown) or a conventional physical foot switch (not shown) connected to the surgical equipment 22.

By interacting with the projected image 27 of the virtual control panel 26, the surgeon's finger 30 and hand remains in the sterile field because the surface upon which the projected image 27 is displayed is sterilized. The virtual foot switch 28 makes it possible to entirely eliminate the physical presence of a typical physical foot switch (not shown) and the typical physical cabling (also not shown) which connects the physical foot switch to the surgical equipment. Because the foot switch 28 is virtual, there are no physical items beneath an operating table 38 which might introduce pathogens into the operating room and create clutter or a risk of tripping surgical personnel as they move about within the operating room 24. The projected image 29 of the foot switch can be located relatively easily beneath the operating table 38 at a position most beneficial to the surgeon 34 when performing a surgical procedure on a patient 40 who is lying on the operating table 38. More than one virtual foot switch 28 may be created to accommodate other surgeons 34 who might also be standing at different positions around the operating table 38 while working on the patient 40.

In addition to controlling the surgical equipment 22, the virtual integration or control system 20 includes a system display 42 which projects information in a system display image 43. The information presented in the system display image 43 may describe the control, status and functionality of the virtual control system 20 and the surgical equipment 22, and/or the physical condition of the patient 40. Information describing the control, status and functionality of the virtual control system 20 is communicated from the system controller 36 (FIGS. 2 and 3), and information describing the control, status and functionality of the surgical equipment 22 is communicated from the surgical equipment 22 to and through the system controller 36 to the system display 42. Information describing the physical condition of the patient is obtained from conventional patient monitoring equipment 44 attached to the patient 40, and the information from the patient monitoring equipment 44 is communicated to and through the system controller 36 to the system display 42.

The system display 42 projects the system image 43 on a surface which is conveniently viewed by the surgeon and the operating room personnel, such as a wall 46 of the operating room 24 or on drapes 48 which cover the patient 40 on the operating table 38, as shown in FIG. 1. In addition, the system information of the system image 43 may also be presented on a conventional monitor 49 which is electrically connected as an output device to the system controller 36. In general, the control, status and functionality information for the surgical equipment 22, and the condition information from the patient monitoring equipment 44, will generally be that type of information which is available on conventional front panels and monitors associated with the equipment 22 and 44.

Some or all of the system information presented by the system display 42 may also be presented by a heads up display 50, which is created by projecting a heads up image 51 onto a conventional face shield 52 worn by the surgeon 34. Projecting the information as a heads up image 51 of the heads up display 50 permits the surgeon to view and consider the information without diverting his or her gaze away from the surgical site. The system display 42 and the heads up display 50, and information on the monitor 49, may be presented simultaneously to permit all of personnel in the operating room 24 to observe that information.

Information concerning the virtual integration or control system 20 itself may be presented on the system display 42, the monitor 49 and/or the heads up display 50. The virtual control system information may include the status, control and functionality information relative to each of the various functions and components of the virtual control system 20. The control system information is useful in confirming the proper functionality of the virtual control system 20.

The surgeon 34 is identified by the virtual control system 20, as a result of the surgeon 34 wearing a surgeon identification tag 54 in an observable position. The surgeon identification tag 54 presents a code, such as a conventional bar code, which uniquely identifies the particular surgeon and distinguishes that surgeon from others who may use the operating room 24. A patient identification tag 56 containing a code identifying the patient 40 and describing the type of surgical procedure to be performed on the patient 40 is placed in an observable position on the patient, such as on the surgical drapes 48 which cover the patient or on an exposed observable part of the patient, such as a wrist or forehead. The virtual control system 20 scans the tags 54 and 56 and obtains the necessary information to establish initial functional settings and conditions of the surgical equipment 22 according to the specific preferences of the surgeon and according to the type of procedure to be performed. In this manner, the surgical personnel are relieved of the responsibility of setting up the surgical equipment 22, and the surgeon is relieved of the requirement to remember his or her preferred settings for the surgical equipment 22 according to the type of procedure to be performed. The information obtained by scanning the tags 54 in 56 may also be displayed as a part of the system display image 43 or the heads up display image 51. The system display 42 and/or the heads up display 50 may also present information describing the type of surgical procedure to be performed on the patient and under appropriate circumstances, the location where that procedure is to be performed, such as on the right or left knee, for example.

A foot position tag 58 (FIGS. 1 and 6) may be attached to a shoe cover 60 of the surgeon 34. The foot position tag 58 is interrogated to locate the position of the surgeon's foot 32 relative to the projected image 29 of the foot switch. The position of the surgeon's foot 32 relative to the foot switch image 29 may be presented on the heads up display 50 or on the system display 42. Presenting the relative position information on the heads up display 50 permits the surgeon 34 to locate the position of his or her foot 32 relative to the projected foot switch image 29 underneath the operating table 38 by viewing the relative positions presented by the heads up display 50 and/or by the system display 42. The surgeon need not divert his attention from the surgical site to look under the operating table 38 in order to locate the projected image 29 from the virtual foot switch 28. The position of the surgeon's foot, as identified by the foot position tag 58, may also be used by the virtual foot switch 28 to project the foot switch image 29 adjacent to the surgeon's foot. In this manner, surgeon need not attempt to locate the foot switch image 29 because it will always be located adjacent to his or her foot. In addition, the location of the foot switch image 29 may be positioned to the left or to the right of the surgeon's foot, according to the preference of the surgeon. The position tag 58 may also serve as the surgeon identification tag 54, under some circumstances.

The tags 54, 56 and 58 are preferably created by a tag generator or printer 62. The bar code or other content information printed on each tag 54, 56 and 58 may be obtained from a memory (not shown) of the system controller 36, or may be supplied from a typical input device 64, such as a keyboard (not shown) attached to the system controller 36. Printing the information on the tags 54, 56 and 58 is controlled by the system controller 36. In this manner, new and replacement tags may be created quickly if necessary prior to or during the surgical procedure. The tag printer 62 is a specific example of a more general type of output device 66 connected to the system controller 36.

The information from the surgeon identification and patient identification tags 54 and 56 is scanned or read and changed into electrical signals by a conventional scanner 68. The system controller 36 controls the operation of each scanner 68 to obtain information from the tags 54 and 56. The scanner 68 is a specific example of a more general type of input device 64 connected to the system controller 36.

Other types of output devices 66 may be connected to the system controller 36 for the purpose of obtaining information from the virtual control system 20. For example, one type of output device 66 may be a data transfer port which permits information concerning the surgical procedure at each point in time during the duration of the procedure to be transferred to a central storage unit for later use or analysis. In this regard, the input and output devices 64 and 68 may function jointly as a connection to a communication network where the information previously discussed may also be distributed outside of the operating room 24.

As shown in FIG. 2, communication links 74 are established between the system controller 36 and the various components and functions of the virtual control system 20. The communication links 74 are preferably optical paths, but the communication links may also be formed by radio frequency transmission and reception paths, hardwired electrical connections, or combinations of optical, radio frequency and hardwired connection paths as may be appropriate for the type of components and functions obtained by those components. The arrows at the ends of the links 74 represent the direction of primary information flow.

The communication links 74 with the surgical equipment 22, the virtual control panel 26, the virtual foot switch 28 and the patient monitoring equipment 44 are bidirectional, meaning that the information flows in both directions through the links 74 connecting those components and functions. For example, the system controller 36 supplies signals which are used to create the control panel image 27 from the virtual control panel 26 and the foot switch image 29 from the virtual foot switch 28. The virtual control panel 26 and the virtual foot switch 28 supply information to the system controller 36 describing the physical interaction of the surgeon's finger 30 and foot 32 (FIG. 1) relative to the projected control panel image 27 and the projected foot switch image 29. The system controller 36 responds to the information describing the physical interaction with the projected images 27 and 29, and supplies control signals to the surgical equipment 22 and patient monitoring equipment 44 to control functionality of those components in response to the physical interaction information. The control, status and functionality information describing the surgical equipment 22 and patient monitoring equipment 44 flows to the system controller 36, and after that information is interpreted by the system controller 36, it is delivered to the system display 42, the monitor 49, and/or the heads up display 50 for presentation.

The communication links 74 between the system controller 36 and the system display 42, the heads up display 50, the monitor 49, the tag printer 62 and the output devices 66 are all uni-directional, meaning that the information flows from the system controller 36 to those components and functions. In a similar manner, the communication links 74 between the system controller 36 and the scanner 68 and the input devices 64 are also unidirectional, but the information flows from the components 68 and 64 to the system controller 36. In certain circumstances, certain control and status information may flow between the system controller 36 and the components 42, 49, 50, 62, 64, 66 and 68 in order to control the functionality of the those components.

Each communication link 74 preferably has a unique identity so that the system controller 36 can individually communicate with each of the components of the virtual control system 20. The unique identity of each communication link is preferable when some or all of the communication links 74 are through the same medium, as would be the case of optical and radio frequency communications. The unique identity of each communication link 74 assures that the system controller 36 has the ability to exercise individual control over each of the components and functions on a very rapid and almost simultaneous manner. The unique identity of each communication link 74 can be achieved by using different frequencies for each communication link 74 or by using unique address and identification codes associated with the communications transferred over each communication link 74.

The functional aspects and interrelationship of the components used in the virtual integration or control system 20 are illustrated in FIG. 3. The system controller 36 has a processor with memory containing an operating program to perform the functions described herein, as well as for storing information. The system controller 36 is connected to the other components of the virtual control system 20 through a conventional system bus 76 to enable communication with and control over those other system components. The system controller 36 transmits and receives the control, status, functionality and condition information over bus 76 and the communication links 74 (FIG. 2), thereby establishing the control and flow of information within the virtual control system 20. The system controller 36 functions as a computer with a processor and memory for storing program and data information to create the functionality of the virtual integration or control system 20.

To establish a wireless bidirectional communication link 74 (FIG. 2) to some of the components, a conventional transceiver 78 is connected to the system bus 76 and a corresponding transceiver 80 is connected to the component, as shown in FIG. 3. Each transceiver 78 and 80 contains a radio frequency or optical transmitter (Tx) and a receiver (Rx), thus making each transceiver 78 and 80 capable of transmitting and receiving information. The transceivers 78 and 80 communicate with each other by transmitting optical or radio frequency signals to establish a wireless communication path as a part of the communication link 74 (FIG. 2) between the system controller 36 and the system component to which the transceiver 80 is connected. In this manner, control, status, functionality and condition information may be transferred between the system controller 36 and the components of the virtual control system 20 without requiring those components to be physically connected by electrical cables to the system controller 36.

A wireless portion of the communication link 74 (FIG. 2) is established by the transceivers 78 and 80, between the system controller 36 and the surgical equipment 22, the patient monitoring equipment 24, a projector sensor 82 of the virtual control panel 26, a projector sensor 84 of the virtual foot switch 28, a projector 86 of the system display 42 and a projector 88 of the heads up display 50. To the extent that the information flows only from the system controller 36 to the system display 42 and the heads up display 50, the transceivers 78 and 80 connected between the system controller 36 and those components 42 and 50 may be replaced by a transmitter and a receiver, respectively.

The monitor 49, the tag printer 62 and other types of output devices 66 may be directly connected to the system bus 76 as shown in FIG. 3, or transceiver or transmitter-receiver pairs (not shown in FIG. 3) may be interposed between the system bus 76 and those components. Similarly, the scanners 68 and other types of input devices 64 may be directly connected to the system bus 76 as shown in FIG. 3, or transceiver or a receiver-transmitter pairs (not shown in FIG. 3) may be interposed between the system bus and those components. To the extent that the surgical equipment 22, the patient monitoring equipment 44, the virtual control panel 26, the virtual foot switch 28, the system display 42, and the heads up display 50 need not be physically separated from the system controller 36 by a wireless communication link 74 (FIG. 2), those components can also be directly electrically connected to the system bus 76.

The virtual control panel 26 and the virtual foot switch 28 use the projector sensors 82 and 84 to create and project the front panel image 27 (shown in FIG. 5) and the foot switch image 29 (shown in FIG. 6) and to interrogate the interaction of the surgeon's finger 30 with the front panel image 27 and the interaction of the surgeon's foot 32 with the foot switch image 29, respectively. The projector sensors 82 and 84 project the images 27 and 29, respectively, in response to control signals supplied by the system controller 36 and from programmed information within each projector sensor.

The interrogated interaction of the surgeon's finger 30 and foot 32 with the images 27 and 29, respectively, results in the delivery of interaction signals over the system bus 76 to the system controller 36 indicating the fact and degree of the interaction.

Figure 4:
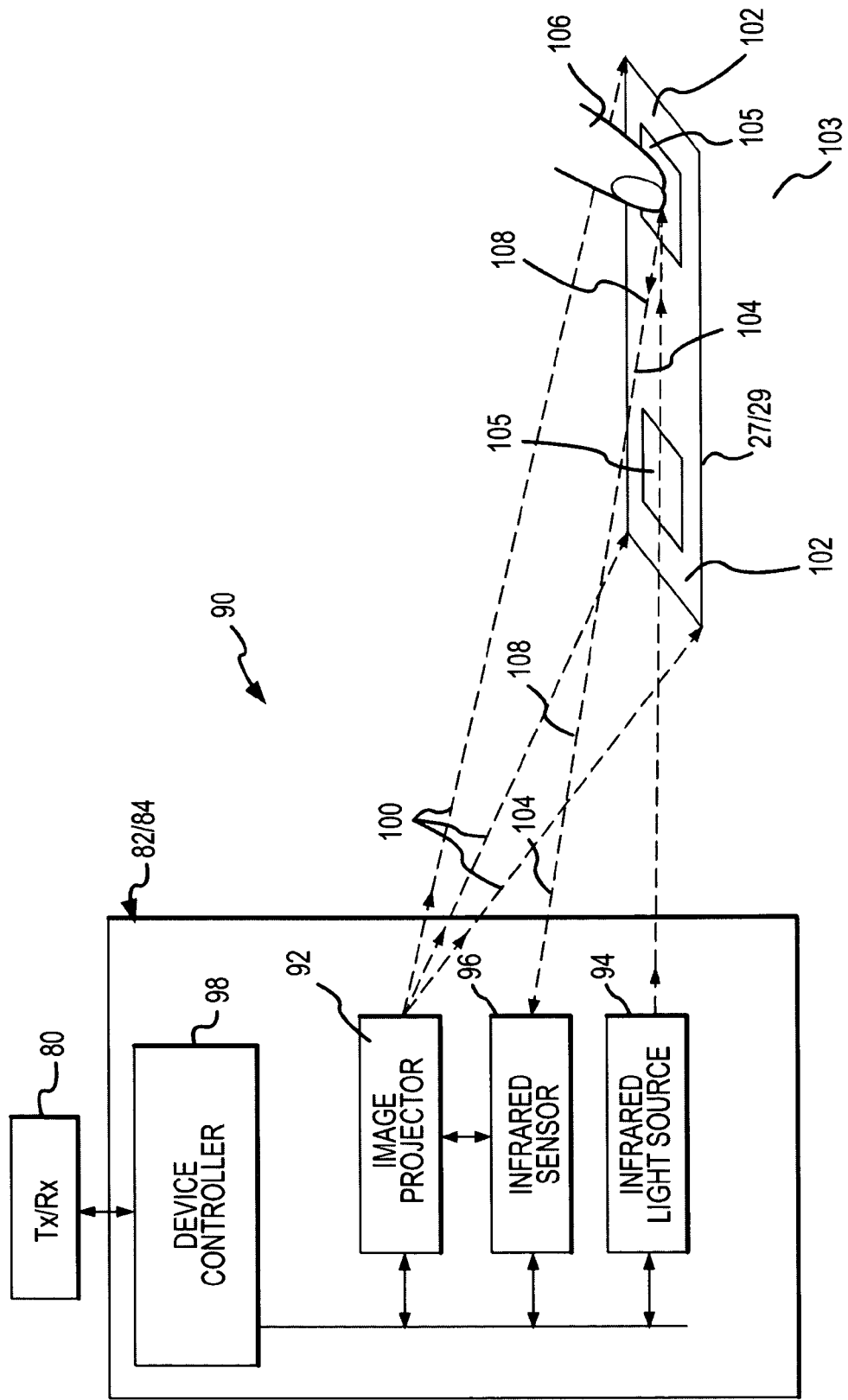
FIG. 4 is a functional block diagram of a virtual control device exemplary of a virtual control panel and a virtual foot switch shown in FIG. 3, also showing interaction by a finger with an image created by the virtual control device.

The virtual control panel 26 and the virtual foot switch 28 are exemplary of virtual control devices which are used with the virtual control system 20. A generic form of a virtual control device 90 is shown in FIG. 4. The components of the generic virtual control device 90 and their functionality are applicable to the virtual control panel 26 and the virtual foot switch 28. The virtual control device 90 uses similar components which function similarly to a virtual keyboard device manufactured by Canesta of San Jose, Calif.

Figure 5:
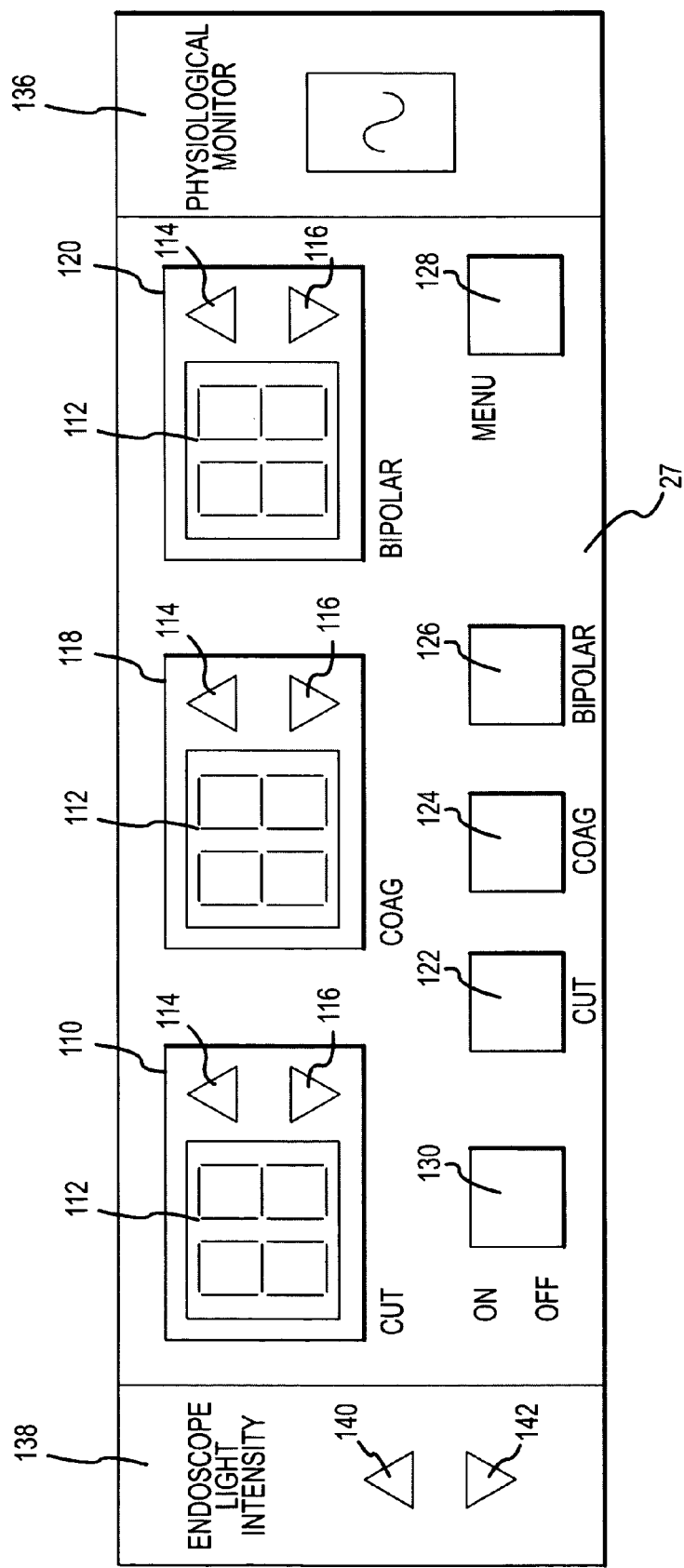
FIG. 5 is an illustration of a projected image of a virtual front control panel shown in FIGS. 1-3.
Figure 6:
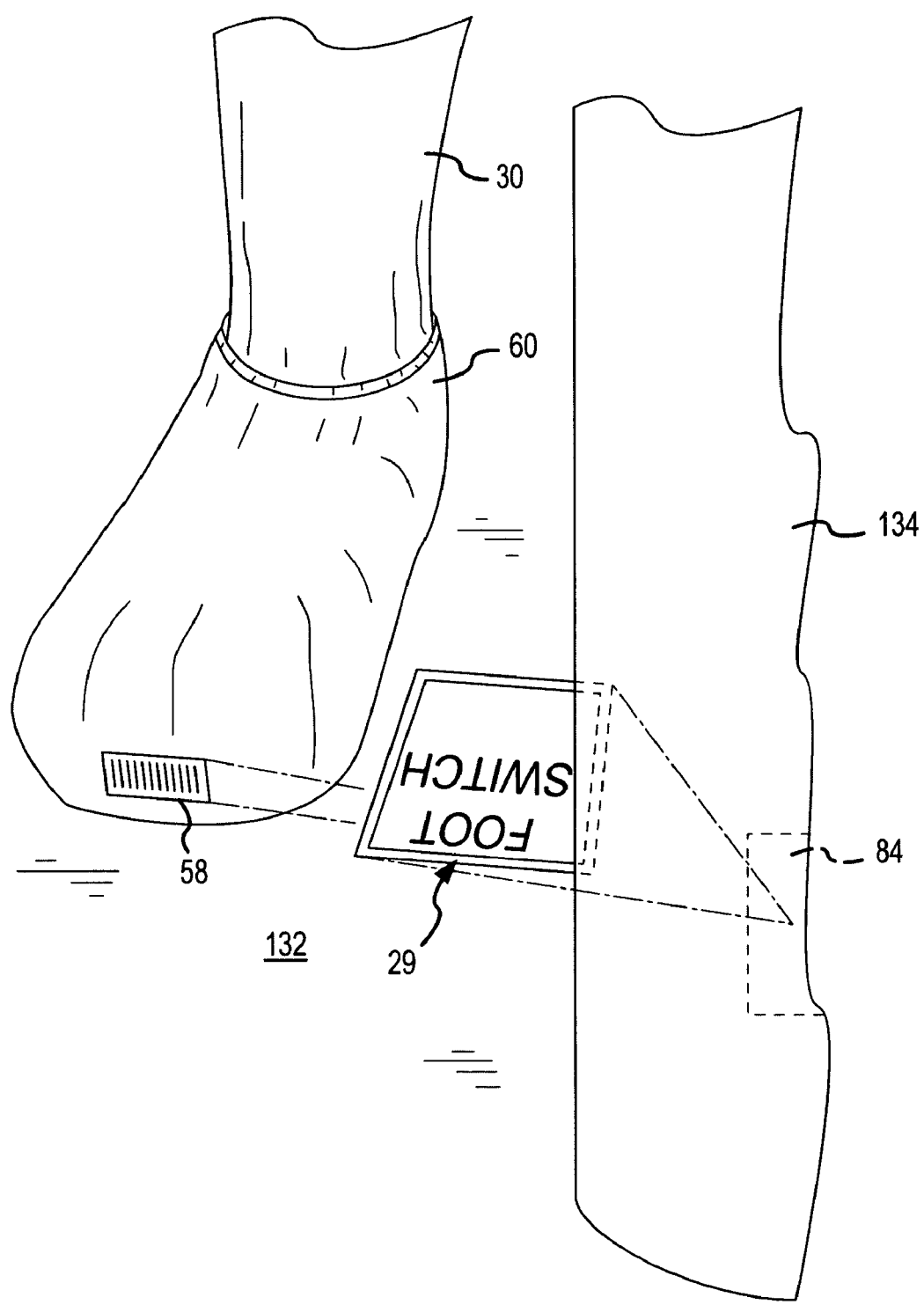
FIG. 6 is an illustration of a projected image of a virtual foot switch shown in FIGS. 1-3, and a perspective view of a surgeon's foot with a position tag attached to a shoe cover interacting with the projected image.

The virtual control device 90 includes an image projector 92, an infrared light source 94, an infrared sensor 96, and a microprocessor-based device controller 98 which functions as a computer with memory. The elements 92, 94, 96 and 98 form the projector sensors 82 and 84 of the virtual front panel 26 and the virtual foot switch 28 (FIG. 3). The image projector 92 projects a light beam 100 which scans and creates the geometric pattern of a projected image 102 that preferably corresponds to the control panel image 27 of the virtual control panel 26 or the foot switch image 29 of the virtual foot switch 28 (FIGS. 5 and 6). The light beam 100 from the image projector 92 scans the image 102 generally onto a surface 103 upon which the image 102 is projected. Scanning of the light beam 100 occurs rapidly, causing the image 102 to appear whole to the viewer, even though only a small portion of the image 102 is actually illuminated by the light beam 100 at each time instant. The scanning angle of the light beam 100 relative to the surface 103 is sufficient to avoid an object 106 blocking the light beam 100 from the image projector 92 until that object 106 comes close to touching the surface 103 upon which the image 102 is projected.

Control information supplied from the device controller 98 to the image projector 92 establishes the scanning pattern of the light beam 100 and hence the geometric pattern of the projected image 102. Control signals from the system controller 36 (FIG. 3) are delivered to the device controller 98 to establish the geometric pattern characteristics of the projected image 102, or alternatively the memory of the device controller 98 may be programmed to define a desired type of projected image 102. The projected image 102 includes a number of contact control areas 105. Touching or contacting a contact control area 105 results in the virtual control device 20 generating an interaction signal which is supplied by the virtual control device 90 to the system controller 36. In response, the system controller 36 delivers a control signal to the surgical equipment 22 (FIG. 3). The communication between the system controller 36 and the device controller 98 is through a communication link 74 (FIG. 2) which may include a transceiver 80 as previously described.

An infrared light beam 104 is transmitted from the infrared light source 94 onto the projected image 102. The scanning angle of the infrared light beam 104 relative to the surface 103 is shallower than the scanning angle of the light beam 100 which creates the image 102. The device controller 98 also controls the infrared light source 98 to scan the projected image 102 with the light beam 104. Preferably, the transmitted light beam 104 is synchronized or coordinated with the geometric pattern of the projected image 102, causing the light beam 104 to sweep or scan the same portion of the projected image 102 that is being simultaneously created by the light beam 100 scanned from the image projector 92. When an interactive object 106, such as the surgeon's finger shown in FIG. 4, approaches a contact control area 105 of the projected image 102, light from the transmitted beam 104 is reflected from the object 106 as a reflected infrared light beam 108. The infrared sensor 96 receives the reflected light beam 108, and signals the device controller 98 of the receipt of the reflected light beam 108.

The infrared light beam 104 transmitted from the infrared light source 94 is a series of pulses of infrared light. The reflected light beam 108 is also a series of pulses of infrared light, because the reflected light beam 108 is created by the transmitted light beam 104. The time between the delivery of the pulses of the transmitted infrared light beam 104 and the receipt of the corresponding pulses of the reflected infrared light beam 108 is calculated by the device controller 98. This relative timing information establishes the distance of the object 106 in contact with the contact control area 105 from the infrared light source 94 and the infrared sensor 96, in a manner similar to the manner that radar establishes the distance to an object. The horizontal position of the object 106 within image 102 is established by the horizontal plane scanning angle of the transmitted light beam 104 which caused the light beam 108 to be reflected by the object. The horizontal plane scanning angle of the light beam 104 is synchronized or coordinated with the creation of the image by the projected beam 100.

By using the distance to the object 106 established by the relative timing information between the corresponding pulses of the transmitted and received light beams 104 and 108, and by using the horizontal scanning angle of the beam 104 which caused the reflection beam 108, both of which are determined and controlled by the device controller 98, the point of interaction of the object 106 with the geometric pattern of the image 102 is established or interrogated. The ability to discriminate interaction of the object 106 with the different contact control areas 105 is thereby obtained. Differentiating between different contact control areas 105 on the projected image 102 assures that the different control functions represented by different contact control areas 105 on the projected image 102 may be separately and individually invoked by bringing the object 106 into contact with those areas 105.

A similar technique of determining the point of interaction of the object 106 with the image 102 could be obtained by using two differently-positioned infrared light sources. Each of the light sources would determine the distance of the object 106 from it. The two different distance would then be used in a triangulation calculation to determine the position of interaction of the object 106 within the image 102 and to thereby interrogate or discriminate the interaction of the object 106 with each of the different contact control areas 105.

Because of the relatively shallow angles of the transmitted and reflected infrared light beams 104 and 108 relative to the surface 103, it is possible to determine when the tip of the object 106 touches the image 102. The shallow angles of the light beams 104 and 108 are not blocked until the object 106 touches the surface 103 or comes relatively close to touching the surface 103. The device controller 98 interprets the light beams 104 and 108 as indicative of contact with the image 102, and thereby formulates the interaction signal. The interaction signal is communicated from the device controller 98 through the transceiver 80 over the link 74 (FIG. 2) to the system controller 36 (FIG. 3). The system controller 36 responds to the interaction signal by delivering control signals through the appropriate link 74 (FIG. 2) to control the surgical equipment 22. In this manner, actual contact of the object 106 with the contact control areas 105 of the projected image 106 of the virtual control device 90 is interrogated and used as a control input interaction to establish control over the surgical equipment 22.

In a similar manner, movement of the object 106 close to or adjacent to the surface 103 without touching the surface can also be discriminated and used as a control input interaction. The relatively shallow angles of the beams 104 and 108 relative to the surface 103 allow the position of the object 106 above the projected image 102 to be derived. A variable control input interaction signal is thereby obtained, with the variation depending upon the distance of the object 106 above the projected image 102. The sensitivity of the distance of the object 106 above the projected image 102 is related to the angle of the reflection beam 108 relative to the surface 103, and may be adjusted by the angle of the infrared sensor 96 relative to the surface 103 or by signal processing within the device controller 98. Adjustments to the sensitivity accommodate the surgeon's preferences for the degree of firmness required to indicate a control input interaction, or to compensate for uneven or irregular surfaces 103.

Other control input interactions may be obtained by movement of the object 106 above the contact control area 105 after having initially contacted the contact control area. For example, lifting the object 106 a slight distance above the contact control area 105 may be interpreted as an additional secondary control input without changing the initial control input derived by having first contacted the object with the contact control area. Lifting the object 106 a further distance above the contact control area 105 could be interpreted as negating the initial control input as well as the secondary control input.

It is also possible to supply interaction control inputs relative to the projected image 102 with a virtual mouse. The virtual mouse results from the surgeon moving his or her finger over the surface 103 upon which the image 102 is projected without losing contact with that surface 103, in much the same way that a cursor is moved on a display monitor by the use of a physical mouse connected to a computer. The transmitted and reflected infrared light beams 104 and 108 (FIG. 4) permit determining the position of the surgeon's finger relative to all of the points which form the projected image 102. The virtual mouse is activated by touching a mouse activation contact control area of the projected image 102, using the virtual mouse in the manner desired to supply interaction input control information or to readjust the position of the display areas or contact control areas 105. Clicking the mouse is achieved by tapping the surface 103 upon which the image 102 is projected by raising and lowering the finger (object 106) with respect to the surface 103 in a predetermined pattern of taps which has been established to indicate a mouse click.

The virtual control device 90, used in the manner just described, becomes the virtual front control panel 26, shown in FIG. 5, and/or the virtual foot switch 28, shown in FIG. 6. Other types of virtual control devices are created and used for control purposes in the same manner.

The control panel image 27 created by the projector sensor 82 (FIG. 3) of the virtual control panel 26 is shown in greater detail in FIG. 5. The control panel image 27 is a substitute for the physical front control panel on the surgical equipment 22 and preferably has the same geometric configuration or layout as the physical front panel. The virtual control panel 26 is also a functional substitute for the functions achieved by the physical front panel of the surgical equipment 22. The virtual control panel 26 will preferably exhibit all of the same functionality as the actual front control panel on the surgical equipment 22. For example, a control panel image 27 for an electrosurgical generator is shown in FIGS. 1 and 5. The projected control panel image 27 includes a number of different contact control areas 105 (FIG. 4). A first portion 110 of the image 27 includes a display portion 112 for displaying the amount of power selected in an electrosurgical cut mode of operation. Contact control areas in the form of up and down arrows 114 and 116 are also presented in the first portion 110. Pressing the arrows 114 and 116 changes the output power from the electrosurgical generator and causes the display portion 112 to display the numerical amount of output power selected. Similar second and third portions 118 and 120 are presented within the projected image 27 to permit control of the power in the coagulation and bipolar modes of operation, respectively. Interacting with the contact control button selection areas 122, 124 and 126 permits the surgeon to select the cut, coagulation and bipolar modes of operation for use, respectively. A contact control menu button area 128 allows the surgeon to select and display other types of information on the control panel image 27, in much the same way that touching a corresponding selection button on the actual control panel of the electrosurgical generator changes the information displayed on it. An on/off contact control button area 130 allows the surgeon to toggle the electrosurgical generator on and off.

The virtual control panel 26 can also display similar or related control information for multiple pieces of surgical equipment 22, and/or for the patient monitoring equipment 44, if desired. Alternatively, additional contact control areas of the projected image 27 may be provided to allow the surgeon to toggle or move between different images 27 of different content. In general, each image 27 will define and include those contact control areas where contact by an object will be interpreted as an input interaction intended to control the surgical equipment.

The surface 103 upon which the virtual control panel image 27 is projected is preferably created by a plate-like device 131 (FIG. 1) which may be sterilized and thereafter placed in the sterile field of the surgical procedure. The projector sensor 82/84 is physically separated from the surface 103 upon which the control panel image 27 is projected, so the projector sensor 82/84 does not need to be sterilized. Consequently, the surgeon can physically interact with sterilized surface 103 of the device 131 upon which the virtual control panel image 27 is projected while remaining within the sterile field to directly control the surgical equipment. As a result, the surgeon need not depend on an assistant to make adjustments to the surgical equipment 22.

The virtual control panel image 27 can also be projected onto the drapes 48 which cover the patient 40 (FIG. 1). However to make the projector sensor 82/84 fully functional in this type of situation, it must be positioned relative to the drapes to permit the transmitted and reflected light beams 104 and 108 to respond to interaction with the projected virtual control panel image 27. Preferably, the virtual control panel image 27 should be projected on a relatively firm surface covered by the drapes 48 to assure effective interrogation resulting from interaction by the surgeon's finger.

Another type of virtual control device 90 (FIG. 4) is the virtual foot switch 28, as shown in FIGS. 1 and 6. The virtual foot switch 28 is created by the projector sensor 84 (FIGS. 3 and 4) projecting the image 29 of a foot switch on the floor 132 beneath the operating table 38. Preferably the projector sensor 84 is attached to a support pedestal 134 of the operating table 38 (FIG. 1). Attached in this manner, the virtual foot switch image 29 can be projected at any desired position on the floor 132 beneath the operating table. Projecting the virtual foot switch image 29 outward from the pedestal 134 avoids obstructions in the line of projection between the projector sensor 84 and the virtual foot switch image 29 and promotes other benefits. The location of the virtual foot switch image 29 on the floor 132 may moved to accommodate shifts in position of the surgeon during the procedure. The projector sensor 184 may create more than one separate virtual foot switch image 29 at different locations beneath the operating table 38. The use of multiple virtual foot switch images 29 accommodates the circumstance where the surgeon moves positions frequently during the surgical procedure, and accommodates the circumstance where multiple surgeons participate in the surgical procedure at different locations around the operating table 38. If necessary or desirable, more than one projector sensor 84 may be attached to different positions on the pedestal 134. The virtual foot switch image 29 can be the size and shape of a regular physical foot switch, or any other size or configuration desired.

Upon the surgeon interacting with the foot switch image 29 by contacting the image 29 with his or her foot 32, the virtual foot switch 28 delivers an interaction signal to the system controller 36 (FIG. 3). The system controller 36 recognizes the interaction signal from the virtual foot switch 28 as an activation command, and the system controller 36 responds by signaling the surgical equipment 22 to commence operation. Upon the surgeon removing his or her foot 32 from contact with the projected foot switch image 29, the virtual foot switch 28 delivers another interaction signal to the system controller 36 (FIG. 3), and the system controller 36 responds by sending a deactivation command to the surgical equipment 22 to cause it to cease operation. In the case where the surgical equipment 22 is an electrosurgical generator, the activation command results in the delivery of output power and the deactivation command causes the electrosurgical generator to cease delivering output power. Because of the relatively shallow scanning angle of the transmitted and reflected infrared light beams 104 and 108 previously described in conjunction with FIG. 4, the surgeon need only lift his or her foot a very slight amount above the surface of the floor 132 to change the state of the control input interaction and thereby change the state of activation or deactivation of the surgical equipment.

To assist the surgeon in interacting with the projected foot switch image 29, the foot position tag 58 is attached to a toe portion near the bottom sole of the shoe cover 60 worn by the surgeon, as shown in FIG. 6. The foot position tag 58 includes a code which is recognized by the infrared sensor 96 (FIG. 4), based on the light which is reflected from that code. By placing the foot position tag 58 on the toe portion of the shoe cover 60 and data location close to the floor 132, the projector sensor 84 and the device controller 98 (FIG. 4) are able to interrogate the position of the foot position tag 58 in much the same manner that the position of the object 106 is determined relative to the projected image 102 (FIG. 4). The information describing the position of the foot position tag 58, and hence the position of the surgeon's foot, is transferred to the system controller 36 (FIG. 3) as an interaction signal. Attaching the projector sensor 84 to the operating table pedestal 134 to project the light outward from the pedestal 134 facilitates reading the information from the foot position tag 58 and interrogating the interaction of the surgeon's foot with the foot switch image 29 because the foot position tag 58 is almost directly facing the projector sensor 84.

The system controller 36 utilizes the foot position information and displays that information for the use by the surgeon. The information is displayed as a representation of the surgeon's foot relative to the projected foot switch image 29 (FIG. 6) of the foot switch. Consequently, the surgeon need not look underneath the operating table 38 and the drapes 48 to attempt to locate and interact with the position of the projected foot switch image 29. Preferably, representation of the surgeon's foot relative to the projected image of the foot switch is displayed on the heads up display 50. In this manner, the surgeon is readily aware of the position of his or her foot relative to the projected foot switch image 29, thereby facilitating using the foot switch in the manner described. The position of the surgeon's foot relative to the projected foot switch image 29 can also be presented as part of the system display 42. Displaying the relative foot position information through the system display 42 is still convenient, although possibly not as convenient as displaying the foot position information through the heads up display 50, because the surgeon can glance at the system display 42 more easily than looking underneath the operating table 38 and raising the drapes 48 to locate the relative position of his or her foot relative to the projected foot switch image 29.

A proximity annunciator (not shown) can also be used to describe the position of the projected foot switch image 29 relative to the surgeon's foot 32. The proximity annunciator responds to the foot position information obtained by interrogating and interpreting the position tag 58 to provide an audible signal having characteristics which indicate the proximity of the surgeon's foot to the projected foot switch image 29. The proximity annunciator could be mobile, battery-powered and connected to the virtual control system 20 through a wireless communication link 74 (FIG. 2) so that the proximity annunciator could be attached to the surgeon's foot to provide essentially the same type of information by creating a physical sensation on the surgeon's foot or leg, such as vibrations or pressure. A characteristic of the sensations indicates the relative distance between the surgeon's foot and the projected foot switch image 29. Use of such a proximity annunciator relieves the surgeon of glancing at any type of visual display to obtain proximity information.

The foot position information derived from the foot position tag 58 can be used to cause the image projector 92 (FIG. 4) to project the foot switch image 29 in a position relative to the location of the surgeon's foot, such as laterally adjacent to the surgeon's foot 30, as shown in FIG. 6. The position of the foot switch image 29 may be either or to the right or to the left of the surgeon's foot, depending upon the surgeon's preference of the location for activating the surgical equipment. Under these circumstances, the surgeon need not be concerned with attempting to locate the foot switch image 29, because the surgeon is assured of contact or interaction with the foot switch image 29 by simply twisting his or her foot at the ankle and stepping down on the floor 132 to contact with the foot switch image 29. The foot position information will not be used to change the position of the image 29 while the surgeon's foot remains interactive with that image 29, such as during times of activation of the surgical equipment. The foot position switch 29 would be repositioned only after interaction with the image 29 had ceased. The surgeon's preference for positioning the foot switch image 29 to the right or to the left of his or her foot can also be accommodated, so that the surgeon is assured interaction is always achieved by movement of the foot to the right or to the left.

An alternative form of the virtual foot switch 28 does not project the visual image 29 of the foot switch, as shown in FIG. 4. Instead a printed image (not shown) of the foot switch is attached to the floor 132 of the operating room 24 beneath the operating table 38. The printed image of the foot switch may be presented on a paper which is attached to the floor 132 with an adhesive. In such a case, the virtual foot switch 28 does not require the use of the image projector 92 (FIG. 4), but does require that the infrared light source 94 project the transmitted light beam 104 precisely relative to the printed image of the foot switch attached to the floor. To locate and identify the characteristics of the printed image, a small flexible tag or other identification, such as a conventional bar code, is printed or placed on the printed image at a predetermined location. Once this identification is observed by the sensor 96, the position of the printed image is determined by the device controller 98 based on the position of that identification.

Information concerning the entire virtual integration or control system 20 is presented on the system display 43 by the system display 42, as shown in FIGS. 1-3. The projector 86 of the system display 42 is connected to the system bus 76 and responds to signals supplied by the system controller 36 to create the system display image 43. The system display image 43 is projected by light emitted from the projector 86 onto the wall 46 of the operating room 24 (FIG. 1), or onto a screen (not shown) that may be set up at any location within the operating room 24 which is convenient for viewing by the surgeon and the operating room personnel. Any or all of the control, status, functionality and condition information may be presented by the system display 42 through the system display image 43.

The projector 88 (FIGS. 1 and 3) of the heads up display 50 is also conventional, but is preferably miniaturized, battery-powered and attached relative to the face shield 52 to project the heads up image 53 on the face shield 52. The typical face shield 52 has a clear plastic lens that protects the face of the surgeon from blood and another biological material that might become airborne during the surgical procedure, but which allows the surgeon to view the surgical site. In this manner, the projector 88 projects the heads up image 53 on the face shield 52 in such a manner that the information can be read while the surgeon also views the surgical site. The information presented by the heads up display 50 may be the same as that information provided on the system display 42. However, in most circumstances, the amount of information provided by the heads up display 50 will be reduced to the most important or critical information which should be viewed by the surgeon without distraction. The surgeon can readily glance up to the system display image 43 to obtain the other less critical or less important information. To establish a communication link 74 (FIG. 2) with the system controller 36 (FIG. 3), a transceiver 80 (FIG. 3) will also be attached to the projector 88 and the face shield 52.

Selected information may also be displayed in conjunction with the control panel image 27, as shown in FIG. 5. For example, patient condition information can be displayed in the area 136 and additional control panel capabilities for other surgical equipment may be displayed in the area 138, with both areas 136 and 138 adjacent to the control panel image 27. Critical or selected patient condition information is presented in the area 136, along with designations describing the type of information presented. Contact control areas 140 and 142 may be presented for the other surgical equipment in the additional control panel area 138. For example, the panel control area 138 may represent the ability to control the intensity of light from an endoscope, and the arrow contact control areas 140 and 142 may be touched to increase and decrease, respectively, the intensity of light emitted from the endoscope. As another example, in the circumstance of the surgeon using an electrosurgical generator near a nerve bundle, the control panel display 27 would display the power setting of the electrosurgical generator at 112, the contact control areas 114 and 116 allow the power setting of the electrosurgical generator to be adjusted, and the area 136 would display the degree of nerve stimulation from a physiological monitor connected to the patient.

Figure 7:
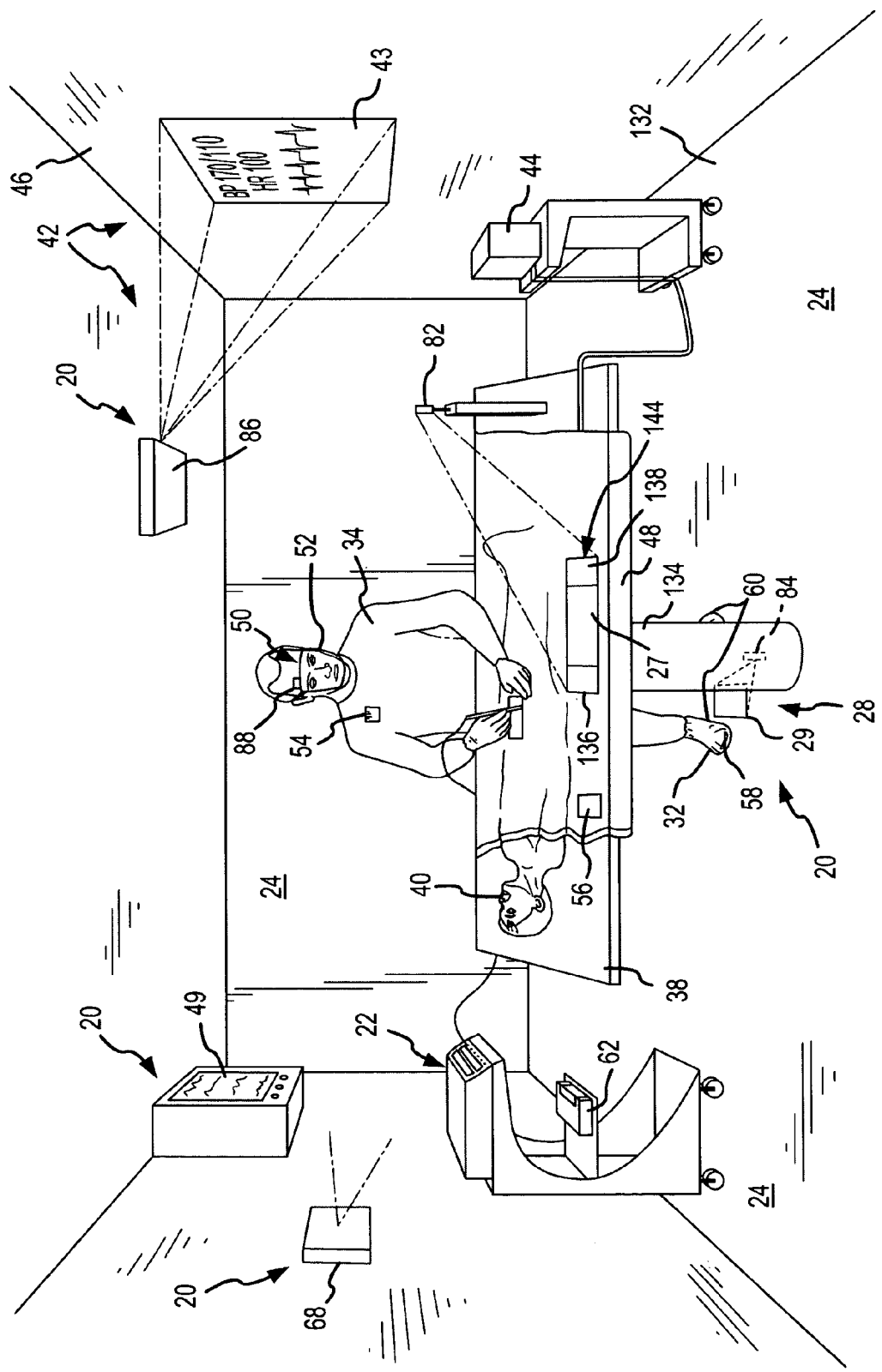
FIG. 7 is a perspective view similar to FIG. 1 showing an alternative form of a control panel and patient information display used in the system.

In addition to, or as an alternative to, displaying information on the plate like device 131 as shown in FIG. 1, the information presented may be presented in an image 144 displayed on the drapes 48 which cover the patient 40 on the operating table 38, as shown in FIG. 7. The image 144 on the drapes 48 is preferably displayed close to the surgical site. With the information presented in this manner, the surgeon can view the selected patient condition information with peripheral vision while working at the surgical site and not diverting attention away from the surgical site. In a somewhat similar manner, the surgeon can also interact with the image 144 to control the surgical equipment in the manner previously described.

Figure 8:
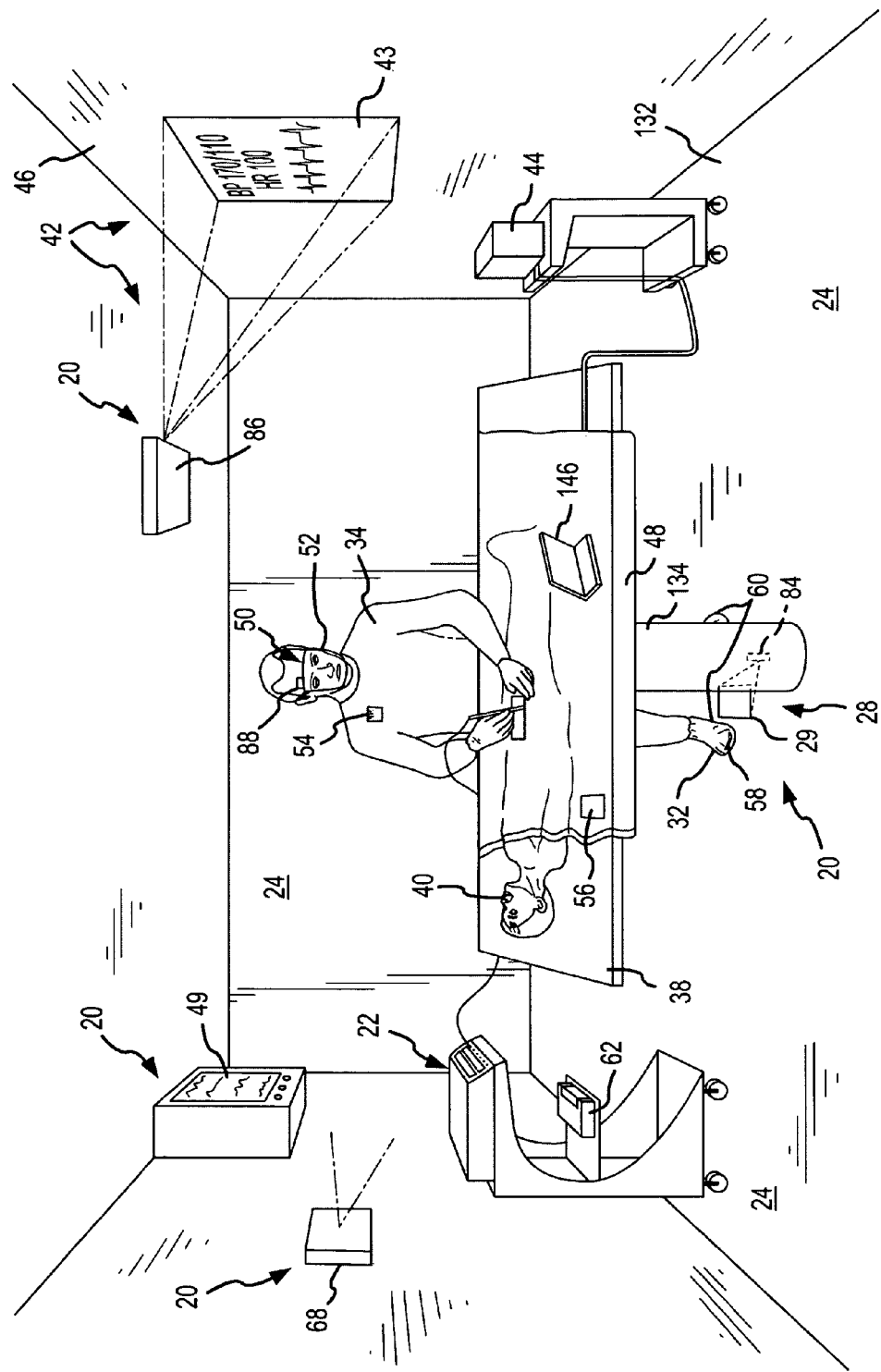
FIG. 8 is a perspective view similar to FIGS. 1 and 7, showing a device which constitutes another alternative form of a control panel and patient information display used in the system.

Another type of display which may be used with the present invention is an integrated information display and control device 146, shown in FIG. 8. The display and control device 146 includes the components discussed in conjunction with FIG. 4, and are located within a sealed housing that has an external surface capable of being sterilized. Under these circumstances, the device 146 may be placed within the sterile field. Clear lenses in the housing are provided to project and receive the light beams 100, 104 and 108 (FIG. 4) that create and interrogate the images on the device 146. The components within the device 146 include a battery to power those components for a time duration sufficient to accomplish the surgical procedure. The device 146 may or may not be reusable. If not reusable, the device 146 is disposed of after concluding the surgical procedure. Placing the device 146 adjacent to the surgical site allows the surgeon to view the information presented on the device 146 and to control the surgical equipment from the device 146 in such a manner that the surgeon's attention is not diverted from the surgical site.

The information contained in the system display image 43 may also be presented on the monitor 49 (FIGS. 1 and 3). As shown in FIG. 3, the monitor 49 is connected to the system bus 76. The information displayed on the monitor 49 is controlled by the system controller 36. By use of the monitor 49, it may not be necessary to use the system display 42, although the monitor 49 and the system display 42 may both be used, or status, control, functionality and condition information may be divided for display by the system display 42 and on the monitor 49.

The virtual control system 20 uses one or more conventional scanners 68 to scan the operating room 24 and read information from the surgeon tag 54 and the patient tag 56, as shown in FIGS. 1-3. The information encoded on the surgeon tag 54 identifies the surgeon. The information may also describe the surgeon's preferences for the settings of the surgical equipment 22 which that surgeon will use to perform the procedure. The surgeon tag 54 is worn on the surgeon's gown, cap, shoe covers, or writs. The information encoded on the patient tag 56 identifies the patient, and the surgical procedure to be performed on the patient. The patient tag 56 is either attached to an exposed portion of the patient or is attached to the surgical drapes 48 which cover the patient 40 on the operating table 38.

The information obtained by each scanner 68 is as a result of scanning the surgeon tag 54 and the patient tag 56. Each tag 54 or 56 includes an optical code, such as a conventional bar code, which can be read when scanned with a conventional laser beam scanner. The code may also be formed by a magnetic or electromagnetic strip that returns information when interrogated by a magnetic or electromagnetic scanner. Each scanner 68 is therefore conventional for interrogating the information encoded into the tags 54 and 56.

The position tag 58 attached to the surgeon's shoe cover 60 (FIG. 6) may also function as, and contain the same information as, the surgeon tag 54. In such a case, the infrared light source 94 and sensor 96 of the virtual control device 90 (FIG. 4) obtain the surgeon identification information from the position tag 58 and supply that information to the system controller 36 (FIG. 3).

The information obtained by the scanner 68 is transmitted over the system bus 76 to the system controller 36, as shown in FIG. 3. The system controller 36 responds to the information scanned from the tags 54 and 56 to obtain numerous beneficial functions. Identifying the surgeon from the information from the surgeon tag 54 and recognizing the particular type of procedure to be performed from the information from the patient tag 56 allows the system controller 36 to establish the surgeon's preferred settings for the surgical equipment 22 for that particular surgical procedure. The system controller 36 may be programmed with information which describes each surgeon's preferred settings of the surgical equipment according to the type of procedure performed. Using the surgeon's identity and preferred settings information permits the system controller 36 to preset the surgical equipment to the surgeon's preferred settings. Alternatively, the information describing the surgeon's preferred settings may be encoded on the surgeon tag 54. Presetting the equipment in this manner relieves the operating room personnel of doing so by memory, and also relieves the surgeon from remembering his or her preferred settings for particular procedures.

The system controller 136 may also be programmed with information which describes the maximum power or other control limits of some or all of the surgical equipment used in the procedure, or this same information may be contained in the information scanned from the information tags 54, 56 or 58. Using this information, the constraints for operating the surgical equipment for a particular procedure will be automatically established, thereby relieving the surgeon and the operating room personnel from the responsibility of setting these operating constraints.

To the extent that all personnel in the operating room are required to wear identification tags similar to the tag 54 worn by the surgeon, the system controller 36 can determine whether only authorized people are present within the operating room. Similarly, the system controller 36 may determine whether the surgeon is authorized to perform the procedure and whether the surgeon is authorized to perform the procedure on the particular patient.

In the case of an emergency circumstance, the normal authorizations for the surgical procedure can be overridden by input information entered into the system controller 36 through an input device 64, such as a keyboard. The overriding information is preferably a password. This overriding capability is useful in case an additional or different surgeon must be brought in to assist on an immediate or emergency basis during the procedure. Without such overriding capabilities, the ability of the additional personnel to assist might be compromised.

In the case where more than one foot switch is connected to a single piece of surgical equipment 22, the information from the surgeon tags 54 allow the system controller 36 to give priority to one of the surgeons if two or more foot switches are activated simultaneously. To the extent that the foot position tag 58 (FIG. 6) also contains information identifying each authorized surgeon, the system controller 36 can determine whether an activation of the surgical equipment is legitimate or accidental. A legitimate activation is determined by interrogation of interaction with the projected foot switch image 29 (FIG. 6) by a foot which has a position tag 58. This arrangement helps to prevent the accidental activation of the surgical equipment by other people in the operating room who may accidentally step onto the projected image of the foot switch or by an object physically encountering the projected image of the foot switch. A similar type of tag worn on the surgical glove of the surgeon also prevents unauthorized individuals from using the virtual control panel 26.

When multiple surgeons use the same surgical equipment, the information from the surgeon identification tags also allow the system controller to change the settings of the surgical equipment in accordance with the particular surgeon who is activating that equipment at any time. Additionally, if more than one piece of surgical equipment 22 is being used, the system controller can assure that each surgeon only activates the particular piece of surgical equipment that the surgeon intends to activate. Similarly, if each of multiple surgeons is to have the capability of activating different surgical equipment, a separate virtual foot switch or virtual control panel for each different piece of surgical equipment may be presented for use by each separate surgeon.

To facilitate the use of the tags 54, 56 and 58, and other similar tags worn by operating room personnel, the tag printer 62 is preferably made part of the virtual control system 20, as shown in FIGS. 1-3. The tag printer 62 is connected to the system bus 76 and is commanded by the system controller 36 to print tags as needed for use. The tag printer 62 permits tags to be created on an immediate basis, to accommodate the operating room personnel and to accommodate changes that might occur during the course of a procedure. Information for printing the tags may be obtained from a keyboard (not shown) or other input device 64, which is connected to the system bus 76, or from information stored in the memory of the system controller 36.

Another feature of the virtual control system 20 is the capability to display an activation indication. The activation indication alerts the surgeon to the activation of a piece of surgical equipment by projecting an indication where it is immediately noticeable to the surgeon, such as on the surgical drape 48 adjacent to the surgical site or as a part of the heads up display 50. The activation indication can also be displayed on the system display 42. The activation indication may also be signaled audibly or physically.

The system controller 36 preferably has a menu capability that allows a user to display different selected information on the displays 42 and 50 and/or as a part of the control panel image 26. The menu capability also allows the user to set up the virtual control system 20 in a preferred manner for use. The input devices 64 and the interrogation and interaction of the surgeon or operating room personnel with the control panel image 27 allow the user to make menu selections and to provide a variety of different functional and set up possibilities. The types of virtual control devices 90 and the type of surgical equipment 22 can be selected and set up for use in preferred manner. Preferences for the settings of the surgical equipment 22 can be entered and stored. The menu option may also provide a graphic of the operating room so that the projected images of each foot switch can be placed where desired.

Additionally, the system controller 36 can also be voice-activated by the use of a microphone forming one of the input devices 64 and by the use of voice recognition software by the system controller 36.

Any type of surgical equipment 22 or patient monitoring equipment 44 may be used with the virtual control system 20, provided that the equipment 22 and 44 includes communication interfaces by which to connect a transceiver 80 or receiver or transmitter. In this way the virtual control system 20 can be used with surgical and patient monitoring equipment made by different manufacturers or equipment that was made prior to the present invention. Moreover, the ability to create the virtual control devices 90 permits any style, type or configuration of control device image 102 to be used in controlling almost any type of surgical equipment. The user of a particular type of surgical equipment is no longer confined to using the type of physical control device supplied with that surgical equipment.

Examples of surgical equipment 22 which may be controlled by the virtual control system 20 include an electrosurgical generator, such as is shown in FIG. 1, as well as other types of devices not shown in FIG. 1, such as laser, ultrasonic and mechanical surgical equipment, optical viewing and imaging equipment, insufflation equipment used in laparoscopic surgery, smoke evacuator equipment, irrigation and aspiration equipment, and essentially any other type of equipment used in an operating room which is controlled or activated by electrical switches and selectors. In each case, however, the surgical equipment 22 should include a communication port or interface by which signals can be communicated to and from that surgical equipment in order to establish its status, condition and functionality.

The patient monitoring equipment 44 is any conventional device used to monitor the physical condition and vital signs of a patient. The patient monitoring equipment 44 should also include a communication port or interface by which signals can be communicated to and from that equipment so as to obtain the condition information presented by the virtual control system 20.

The information content describing the control, status and functionality of the surgical equipment 22 will vary according to the type of surgical equipment 22 which is a part of the virtual control system 20. Similarly, the content of the condition information will vary according to the type of patient monitoring equipment 44 used during the procedure.

Figure 9:
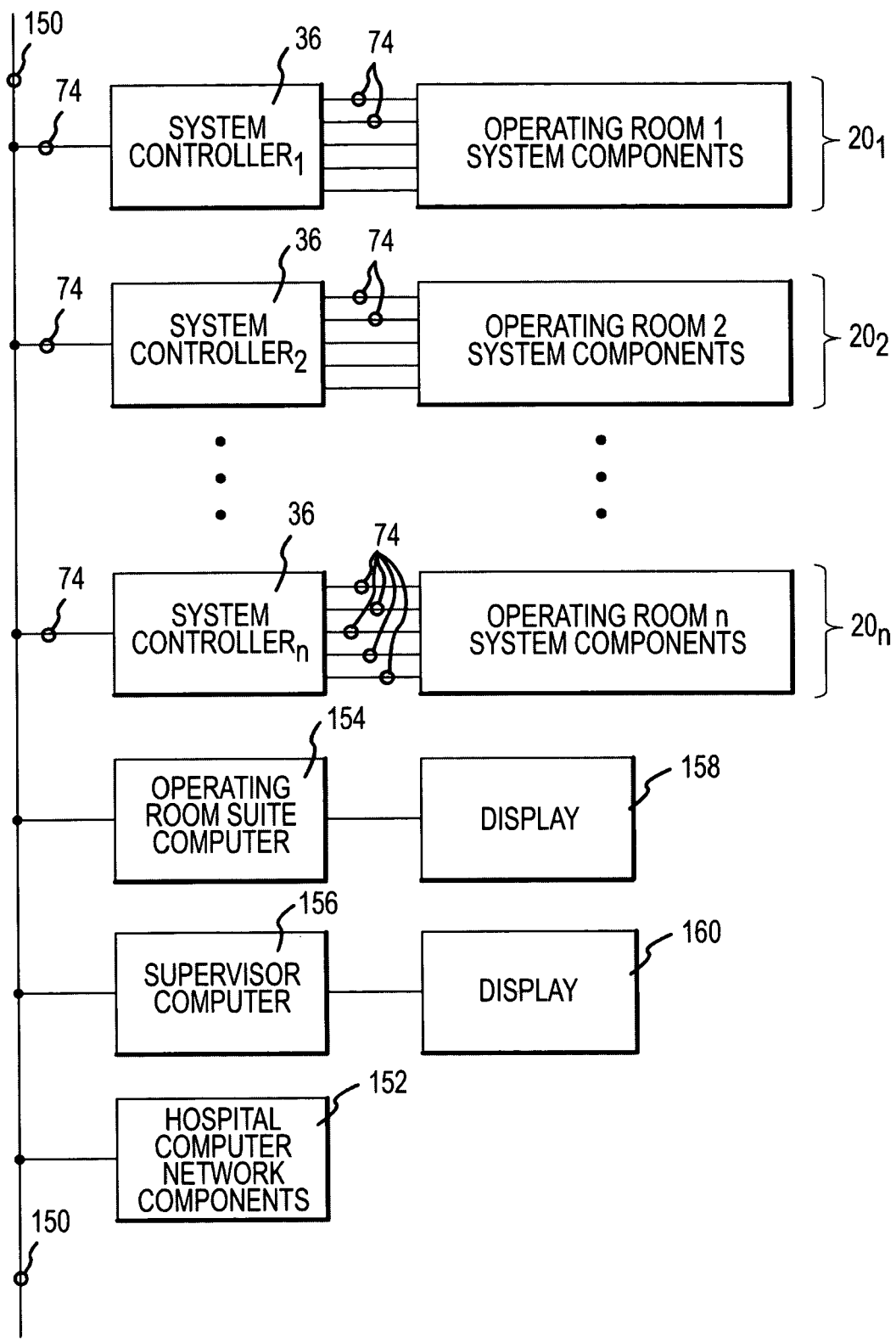
FIG. 9 is a block diagram showing the connection of a plurality of the virtual integration or control and display systems shown in FIGS. 1-8, in a communication network used in a hospital or surgical suite having multiple operating rooms.

As discussed above, one virtual integration or control system 20 is incorporated in an operating room 24 (FIG. 1), and many of the improvements from doing so have been described in conjunction with FIGS. 1-8. Additional improvements and benefits are obtained by interconnecting the integration or control system 20 in a multiplicity of separate operating rooms, in a hospital or surgical suite. As shown in FIG. 9, the system controller 36 of each integrated or control system 20 is connected together with a communication network 150, such as a conventional local area network. The network 150 includes individual communication links 74 between the system controllers 36 and with other components 152 of a hospital computer network, such as and including an operating room suite computer 154 and a supervisor computer 156.

By linking the different virtual integration or control systems 20 through conventional network 150, it is possible for a surgeon who is operating simultaneously on multiple patients to monitor the condition of each of those patients through the displays of information provided at the surgeon's location in any of the operating rooms. It is sometimes the case that one surgeon will not perform the entire surgical procedure, but instead a more junior surgeon may perform some of the less critical aspects of the procedure and the more senior surgeon taking over to perform the most critical aspects of the procedure. Under those circumstances, multiple surgeons may be working on multiple patients simultaneously, but it might still be necessary or desirable for all the surgeons to monitor the individual conditions of all of the patients. Similarly, in certain organ transplant circumstances, the surgical procedures on both the donor and the recipient may occur simultaneously, and it may be necessary or desirable for all the surgeons to monitor the condition of both patients simultaneously.

Another benefit to linking the virtual integration or control systems 20 in each of multiple operating rooms is that a circulating nurse can monitor the location and use of surgical equipment and patient monitoring equipment in each of the operating rooms. One of the primary functions of a circulating nurse is to transfer the certain types of surgical equipment among the operating rooms at the points in the surgical procedures when the equipment is needed, or to obtain certain types of surgical equipment under emergency conditions. A display 158 connected to the operating room suite computer 154 may be used to provide the information describing the location of the equipment to the circulating nurse. Alternatively, any one of the display images presented in any of the operating rooms that are available to be observed by the operating room personnel could be used to quickly display the location of the equipment in the other operating rooms. The ability to display the location of the equipment enhances the ability to locate and use that equipment quickly and efficiently during the procedure.

Similarly, a supervisor of an entire suite of operating rooms within a hospital or other similar institution can monitor the progress of each procedure and utilization of the equipment in each of the operating rooms by using a display 160 connected to the supervisor computer 156. The location of the equipment can also be identified in this manner. Information concerning the use and type of equipment employed in each procedure, as well as the control, status, functionality and condition information relative to the equipment and the patient in each operating room may be recorded in memory by the use of the supervisor computer 156, or a similar other type of computer component 152 connected to the hospital computer. The identity of those individuals present in the operating room can be determined by scanning the information tags within each of the operating rooms. In general, linking a multiplicity of virtual integration or control systems in the manner described provides benefits on an institution-wide basis which are significant to the efficiency of the operational conduct of that institution and to the efficiency with which the surgical procedures are performed.

The benefits and improvements of the virtual integration or control system 20 are numerous and significant. The virtual foot switch 28 avoids the clutter and tripping hazard caused by conventional physical foot switches within the operating room. The virtual control panel 26 allows the surgeon to activate and control the virtual control system 20 without relying on assistance from others, without having to move or adjust the position of the virtual control devices and while maintaining a sterile field. Preferred settings of the surgical equipment can be automatically established. Unauthorized and accidental activations and adjustments to the surgical equipment may be prevented and avoided. The identity of the patient and the type of surgical procedure to be performed may be confirmed, while vital information concerning the patient is presented during the procedure. Multiple virtual control devices can be created and positioned for use, so that more than one surgeon can use them during the surgical procedure. Information concerning the control, status, functionality and location of the equipment, and the condition of the patients in multiple different operating rooms, can be displayed and otherwise used on an institution-wide basis for more efficient management of the institution and performance of surgical procedures. Many other improvements have been described above. Other improvements and advantages will be more apparent after comprehending the full ramifications of the present invention.

Presently preferred embodiments of the invention and many of its improvements have been described with a degree of particularity. This description is of preferred examples of implementing the invention, and is not necessarily intended to limit the scope of the invention. The scope of the invention is defined by the following claims.

The invention claimed is:

1. A virtual control system for controlling surgical equipment in an operating room while a surgeon performs a surgical procedure on a patient, comprising:
a virtual control device including an image of a control device located on a surface and a sensor for interrogating contact interaction of an object with the image on the surface, the virtual control device delivering an interaction signal indicative of the contact interaction of the object with the image; and
a system controller connected to receive the interaction signal from the virtual control device and to deliver a control signal to the surgical equipment in response to the interaction signal to control the surgical equipment in response to the contact interaction of the object with the image.

2. A virtual control system as defined in claim 1, wherein:
the object is one of a finger or a foot of the surgeon;
the image is one of a projected light image or a printed image of a control panel for the surgical equipment;
the image includes at least one contact control area which represents a control function of the surgical equipment; and
the interaction with the image is contact of the object with the contact control area.

3. A virtual control system as defined in claim 2, wherein:
the sensor optically interrogates the contact interaction of the object with the image.

4. A virtual control system as defined in claim 3, wherein:
the optical sensor responds to reflected light from the object interacting with the contact control area to supply a signal indicative of the contact interaction of the object with the contact control area.

5. A virtual control system as defined in claim 4, wherein:
the signal supplied by the optical sensor relates to the degree of separation of the object from contact with the contact control area.

6. A virtual control system as defined in claim 4, wherein:
the virtual control device further comprises a light source which projects incident light onto the contact control area; and
the reflected light is reflected from the incident light by the object interacting with the contact control area.

7. A virtual control system as defined in claim 6, wherein:
the incident light projected from the light source is a pulsed beam of incident light which is scanned through a range of scanning angles over the surface upon which the image is projected;
the reflected light from the object interacting with the contact control area is derived from the pulsed incident light; and
the virtual control device further comprises a device controller connected to the light source and sensor and which is operative to determine contact interaction of the object with the contact control area based on relative timing information between corresponding pulses of the incident light and the reflected light and the scanning angle of the incident light which causes the reflected light.

8. A virtual control system as defined in claim 6, wherein:
the image is a projected light image; and
the virtual control device further comprises an image projector to project a beam of image light to create the image and the contact control area of the image.

9. A virtual control system as defined in claim 8, wherein:
the virtual control device further comprises a device controller connected to the image projector to control the image projector to project the beam of image light through a range of projection angles over the surface to create the image and the contact control area of the image;
the incident light projected from the light source is a pulsed beam of incident light which is scanned through a range of scanning angles over the surface upon which the image is projected;
the reflected light from the object interacting with the contact control area is also pulsed due to reflection of the pulsed incident light;
the device controller is connected to the light source to control the scanning angles of the pulsed beam of incident light in correlation with the projection angles of the beam of image light; and
the device controller interrogates the contact interaction of the object with the contact control area based on the correlated relationship between scanning angles of the incident light and the projection angles of the image light and the relative timing between corresponding pulses of the incident light and the reflected light.

10. A virtual control system as defined in claim 6, wherein:
the virtual control device further comprises an image projector to project image light to create the image and a multiplicity of different contact control areas within the image, each contact control area representing a different control function of the surgical equipment;
the image projector projects the image light in a correlated relationship with the incident light projected by the light source; and
the virtual control device further comprises a device controller connected to the light source, the image projector and the sensor to determine the contact interaction of the object with the contact control area based on a correlation between the incident light and the reflected light and a correlation between the image light and the incident light.

11. A virtual control system as defined in claim 3, wherein:
the object which interacts by contact with the image is a finger of a hand of the surgeon;
the image is located adjacent to a surgical site and within a sterile field; and further comprising:
a position tag attached to the hand of the surgeon; and wherein:
the sensor optically interrogates the interaction of the surgeon's finger with the contact control area and also optically interrogates the position of the position tag; and
the system controller responds to the position of the position tag to permit control of the surgical equipment only in response to the contact interaction of the finger of the hand of the surgeon upon which the position tag is attached with the contact control area.

12. A virtual control system as defined in claim 11, wherein:
the position tag contains information describing at least one of the surgeon, the patient or the surgical procedure to be performed on the patient; and further comprising:
a scanner connected to the system controller and located within the operating room, the scanner reading the information from the position tag; and wherein:
the system controller establishes control over the surgical equipment in response to the information read from the position tag.

13. A virtual control system as defined in claim 12, further comprising:
an identification tag associated with the patient and containing information which describes the patient; and wherein:
the position tag contains information which describes the surgeon;
the system controller accesses information stored in memory which correlates the surgeon and the patient; and
the system controller permits operation of the surgical equipment only in response to the information read from the identification tag and the position tag which correlates the surgeon with the patient.

14. A virtual control system as defined in claim 13, wherein:
one of the position tag or the identification tag contains information describing the surgical procedure to be performed on the patient;
the system controller accesses information stored in memory which describes the surgeon, the patient and the surgical procedure to be performed on the patient; and
the system controller permits operation of the surgical equipment only in response to the information read from the identification tag and the position tag which correlates the surgeon and the patient and the surgical procedure.

15. A virtual control system as defined in claim 2, wherein:
the object is a finger of the surgeon;
the image of the control device is an image of a control panel of the surgical equipment;
the interaction with the image is contact of the surgeon's finger with the contact control area; and the image of the control panel is located within a sterile field of the surgical procedure.

16. A virtual control system as defined in claim 15, wherein:
the sensor optically interrogates contact interaction of the surgeon's finger with the contact control area.

17. A virtual control system as defined in claim 16, wherein:
the image of the control panel includes a multiplicity of different contact control areas, each contact control area representing a different control function of the surgical equipment; and
the sensor optically interrogates the contact interaction of the surgeon's finger with each of the different contact control areas.

18. A virtual control system as defined in claim 17, wherein:
the image is a projected light image;
the virtual control device further includes an image projector which projects the light image of the control panel; and
the virtual control device projects the image of the control panel adjacent to a surgical site and within the sterile field.

19. A virtual control system as defined in claim 2, wherein:
the object is a foot of the surgeon;
the image is located on a floor of the operating room beneath an operating table; and
the interaction with the image is contact of the surgeon's foot with the contact control area.

20. A virtual control system as defined in claim 19, wherein:
the sensor optically interrogates contact interaction of the surgeon's foot with the image.

21. A virtual control system as defined in claim 20, wherein:
the contact control area of the image represents an activation function of the surgical equipment.

22. A virtual control system as defined in claim 21, wherein:
the image is a projected light image; and
the virtual control device further includes an image projector which projects the light image.

23. A virtual control system as defined in claim 22, further comprising:
a face shield worn by the surgeon; and
a heads up projector connected to the system controller and interactive with the face shield to create a heads up display image on the face shield; and wherein:
the system controller is connected to the virtual control device to obtain information describing the position of the projected image of the contact control area relative to the position of the surgeon's foot; and
the heads up projector presents information in the heads up display image on the face shield describing the relative position of the projected image of the contact control area relative to the position of the surgeon's foot.

24. A virtual control system as defined in claim 23, wherein:
virtual control device and the system controller are connected by a wireless communication path;
the system controller and the surgical equipment are connected by a wireless communication path; and
the heads up projector and the system controller are connected by a wireless communication path.

25. A virtual control system as defined in claim 20, wherein:
the image is a projected light image;
the virtual control device further includes an image projector which projects the light image; and further comprising:
a position tag attached to the surgeon's foot; and wherein:
the sensor optically interrogates the interaction of the surgeon's foot with the contact control area and also optically interrogates the position of the position tag; and
the virtual control device supplies the interaction signal only upon contact with the contact control area by the foot to which the position tag is attached.

26. A virtual control system as defined in claim 25, wherein:
the virtual control device responds to the interrogated position of the position tag to control the image projector to project the image of the contact control area on the floor at a position relative to the interrogated position of the position tag.

27. A virtual control system as defined in claim 26, wherein:
the position at which the contact control area is projected on the floor relative to the position tag is laterally adjacent to the surgeon's foot.

28. A virtual control system as defined in claim 26, wherein:
the system controller is connected to the virtual control device to obtain information describing the position of the projected image of the contact control area relative to the interrogated position of the position tag; and further comprising:
a system display comprising a projector connected to the system controller and operative to create a system display image presenting the information describing the position of the projected image of the contact control area relative to the interrogated position of the position tag.

29. A virtual control system as defined in claim 25, wherein:
the system controller is connected to the virtual control device to obtain information describing the position of the projected image of the contact control area relative to the interrogated position of the position tag; and further comprising:
a face shield to be worn by the surgeon; and
a heads up display comprising a heads up projector connected to the system controller and interactive with the face shield to create a heads up display image on the face shield presenting the information describing the position of the projected image of the contact control area relative to the interrogated position of the position tag.

30. A virtual control system as defined in claim 29, wherein:
the surgical equipment supplies information describing the status, control and functionality of the surgical equipment;
the surgical equipment includes patient monitoring equipment which supplies information describing a condition of the patient during the surgical procedure; and
the heads up projector presents information on the face shield describing at least some of the control, status and functionality of the surgical equipment and the condition of the patient.

31. A virtual control system as defined in claim 29, wherein:
virtual control device and the system controller are connected by a wireless communication path;
the system controller and the surgical equipment are connected by a wireless communication path; and
the heads up projector and the system controller are connected by a wireless communication path.

32. A virtual control system as defined in claim 25, further comprising:
a proximity indicator connected to the system controller and responsive to the interrogated position of the position tag relative to the projected image of the contact control area to signal a degree of separation between the position tag and the contact control area.

33. A virtual control system as defined in claim 25, wherein:
the position tag contains information describing at least one of the surgeon, the patient or the surgical procedure to be performed on the patient; and further comprising:
a scanner connected to the system controller and located within the operating room, the scanner reading the information from the position tag; and wherein:
the system controller establishes control over the surgical equipment in response to the information read from the position tag.

34. A virtual control system as defined in claim 33, further comprising:
a patient identification tag associated with the patient and containing information which describes the patient; and wherein:
the position tag contains information which describes the surgeon;
the system controller accesses information stored in memory which correlates the surgeon and the patient; and
the system controller permits operation of the surgical equipment only in response to the information read from the identification tag and the position tag which correlates the surgeon with the patient.

35. A virtual control system as defined in claim 34, wherein:
one of the position tag or the patient identification tag contains information describing the surgical procedure to be performed on the patient;
the system controller accesses information stored in memory which describes the surgical procedure to be performed on the patient; and
the system controller permits operation of the surgical equipment only in response to the information read from the identification tag and the position tag which correlates the surgeon and the patient and the surgical procedure.

36. A virtual control system for controlling surgical equipment in an operating room while a surgeon performs a surgical procedure on a patient, comprising:
an identification tag associated with at least one of the patient or the surgeon, the identification tag containing information describing at least one of the surgeon, a hand of the surgeon, a foot of the surgeon, the patient or the surgical procedure to be performed on the patient;
a virtual control device including an image of a control device and a sensor for interrogating interaction of the surgeon with the control device image and for reading information from the identification tag, the virtual control device delivering an interaction signal indicative of the interaction of the surgeon with the control device image and also delivering information obtained from reading the identification tag; and a system controller responsive to the interaction signal and the information read from the identification tag to deliver a control signal to the surgical equipment to control the surgical equipment only in response to the interaction with the control device image by the surgeon who is described by the information obtained by reading the identification tag.

37. A virtual control system as defined in claim 36, further comprising:

a face shield to be worn by the surgeon; and wherein:

the display image is created by the projector on the face shield.

38. A virtual control system as defined in claim 36, further comprising:

a display comprising a projector connected to the system continuer and operative to create a display image at a location within the operating room removed from the surgical equipment; and a scanner connected to the system continuer and located within the operating room, the scanner reading the information from the identification tag; and wherein:

the system controller responds to the information read from the identification tag to cause the projector to display information related to at least some of the information read from the identification tag.

39. A virtual control system as defined in claim 38, wherein:

the information displayed describes an initial operative setting of surgical equipment to be used in the procedure.

40. A virtual control system as defined in claim 38, wherein:

the information displayed describes the procedure to be performed on the patient.

41. A virtual control system as defined in claim 38, wherein:

the information displayed describes the patient upon which the procedure is to be performed.

42. A virtual control system as defined in claim 38, wherein:

the information displayed describes the surgeon who is to perform the procedure.

43. A virtual control system as defined in claim 36, wherein:

the identification tag is associated with the patient.

44. A virtual control system as defined in claim 36, wherein:

the identification tag is associated with the surgeon.

45. A virtual control system as defined in claim 44, wherein:

the surgeon identification tag is attached to the foot of the surgeon, the surgeon identification tag containing information describing the surgeon; and further comprising:

a scanner connected to the system controller and located within the operating room, the scanner reading the information from the surgeon identification tag; and wherein:

the virtual control device further includes an image projector which projects a light image of the control panel on the floor of the operating room;

the interaction with the control panel image is by the foot of the surgeon; and the system controller responds to the information read from the surgeon identification tag to permit control of the surgical equipment only in response to the interaction with the control panel image of the foot of the surgeon upon which the surgeon identification tag is attached.

46. A virtual control system as defined in claim 45, wherein:

the control panel image includes a control area which represents an activation function of the surgical equipment; and the interaction is of the foot of the surgeon with the control area which represents the activation function.

47. A virtual control system as defined in claim 46, wherein:

the virtual control device controls the image projector to project the control panel image on the floor at a position relative to the position of the surgeon identification tag.

48. A virtual control system as defined in claim 44, wherein:

the surgeon identification tag is attached to the hand of the surgeon, the surgeon identification tag containing information identifying the surgeon;

a scanner connected to the system controller and located within the operating room, the scanner reading the information from the surgeon identification tag;

the virtual control device further includes an image projector which projects a light image of the control panel adjacent to a surgical site within a sterile field;

the interaction with the control panel image is by the hand of the surgeon; and the system controller responds to the information read from the surgeon identification tag to permit control of the surgical equipment only in response to the interaction of the hand of the surgeon upon which the surgeon identification tag is attached with the control panel image.

49. A virtual control system as defined in claim 36, wherein:

an identification tag is associated with each of the patient and the surgeon;

the identification tag is associated with the patient is a patient identification tag; and the identification tag associated with the surgeon is a surgeon identification tag.

50. A virtual control system as defined in claim 49, wherein:

the surgeon identification tag contains information describing at least one of the surgeon, the patient or the surgical procedure to be performed on the patient;

the patient identification tag contains information describing at least one of the surgeon, the patient or the surgical procedure to be performed on the patient; and further comprising:

a scanner connected to the system controller and located within the operating room, the scanner reading the information from the surgeon identification tag and the patient identification tag; and wherein:

the system controller permits operation of the surgical equipment in response to correlation of the information read from the surgeon identification tag and the information read from the patient identification tag.

51. A virtual control system as defined in claim 49, wherein:

at least one of the identification tags containing information identifying the surgeon, the patient or the surgical procedure to be performed on the patient; and further comprising:

a scanner connected to the system controller and located within the operating room, the scanner reading the information from the one identification tag; and wherein:

the system controller establishes control over the surgical equipment in response to the information read from the one identification tag.

52. A virtual control system as defined in claim 51, wherein:

the information from the one identification tag describes the initial operative setting of the surgical equipment; and the system controller responds to the initial operative setting information read from the one identification tag to establish the initial operative setting of the surgical equipment.

53. A virtual control system as defined in claim 51, wherein:

the one identification tag contains information which describes the surgeon and the surgical procedure;

the system controller accesses information stored in memory which correlates the surgeon with the surgeon's preferred initial operative setting of the surgical equipment for the surgical procedure; and the system controller establishes the initial operative setting of the surgical equipment in response to the information read from the one identification tag and the information stored in memory which correlates the surgeon with the surgeon's preferred initial operative selling.

54. A virtual control system as defined in claim 51, wherein:

the one identification tag also contains information which describes the surgical procedure to be performed on the patient;

the system controller accesses information stored in memory which correlates initial operative settings of the surgical equipment with the surgical procedure to be performed on the patient; and the system controller establishes the initial operative settings of the surgical equipment in response to the information stored in memory and the information read from the one identification tag which describes the surgical procedure.

55. A virtual control system as defined in claim 51, wherein:

the identification tag is associated with the surgeon by the surgeon wearing the identification tag.

56. A virtual control system as defined in claim 55, wherein:

the surgeon identification tag is worn by the surgeon on at least one of a surgical gown, a surgical glove or a foot cover.

57. A virtual control system as defined in claim 51, wherein:

the identification tag is associated with the patient by attachment to surgical drapes which cover the patient during the procedure.

58. A virtual control system as defined in claim 51, wherein:

the identification tag is associated with the patient by attachment to the patient's body during the surgical procedure.

59. A virtual control system as defined in claim 51, wherein:

the one identification tag contains information which describes the surgeon and the patient;

the system controller accesses information stored in memory which correlates the surgeon with the patient; and the system controller permits operation of the surgical equipment only in response to the information read from the one identification tag correlating the surgeon and the patient.

60. A virtual control system as defined in claim 51, wherein:

the one identification tag contains information which describes the surgeon;

the system controller permits operation of the surgical equipment only in response to information read from the one identification tag which describes the surgeon; and further comprising:

an input device connected to the system controller by which to supply information to the system controller; end wherein:

the system controller permits operation of the surgical equipment in response to override information supplied to the system controller through the input device if the information read from the one identification tag does not describe the surgeon.

61. A virtual control system as defined in claim 60, wherein:

the override information is a password.

62. A virtual control system as defined in claim 51, wherein:

the one identification tag contains information which describes the surgeon;

the system controller accesses information stored in memory which correlates the surgeon with the surgeon's preferred initial operative setting of the surgical equipment; and further comprising:

a system display comprising a projector connected to the system controller and operative to create a display image presenting the information describing the surgeon's preferred initial operative setting of the surgical equipment.

63. A method for controlling surgical equipment in an operating room while a surgeon performs a surgical procedure on a patient, comprising:

creating an image of a control device for the surgical equipment on a surface;

interrogating interaction of the surgeon by contact with the control device image on the surface; and controlling the surgical equipment in response to the contact interaction of the surgeon with the image on the surface.

64. A method as defined in claim 63, further comprising:

creating at least one contact control area of the control device image; and interrogating contact interaction of one of a finger or a foot of the surgeon with the image on the surface to control the surgical equipment.

65. A method as defined in claim 64, further comprising:

optically interrogating the contact interaction of the surgeon's finger or foot with the image.

66. A method as defined in claim 64, further comprising:

optically interrogating contact interaction with the contact control area by using light reflected from the position of the one finger or foot relative to the contact control area.

67. A method as defined in claim 63, further comprising:

projecting an optical image of a control panel for the surgical equipment on the surface;

including within the projected image of the control panel a contact control area which represents a control function of the surgical equipment; and
optically interrogating contact of a finger of the surgeon with the contact control area of the control panel image to control surgical equipment.

68. A method as defined in claim 67, further comprising:
projecting the image of the control panel within a sterile field of the surgical procedure.

69. A method as defined in claim 67, further comprising:
projecting the image of the control panel on surgical drapes adjacent to a surgical site.

70. A method as defined in claim 67, further comprising:
including in the projected optical image of the control panel a multiplicity of different contact control areas, each contact control area representing a different control function of the surgical equipment; and
optically interrogating the contact interaction of the surgeon's finger with each of the different contact control areas.

71. A method as defined in claim 67, further comprising:
uttering voice commands; and
controlling the image in response to the voice commands.

72. A method as defined in claim 63, further comprising:
using a printed image of the control device to create the image of the control device.

73. A method as defined in claim 63, further comprising:
projecting an optical image of a foot switch of the surgical equipment on a floor of the operating room;
including within the projected image of the foot switch a contact control area which represents an activation control function of the surgical equipment;
optically interrogating contact of a foot of the surgeon with the contact control area of the foot switch image; and
activating the surgical equipment in response to interrogated contact of the foot of the surgeon with the contact control area of the foot switch image.

74. A method as defined in claim 73, further comprising:
attaching a position tag to the surgeon's foot; and
optically interrogating the position of the position tag relative to the contact control area.

75. A method as defined in claim 74, further comprising:
projecting the foot switch image with the contact control area on the floor at a position relative to the interrogated position of the position tag.

76. A method as defined in claim 75, further comprising:
projecting the contact control area on the floor laterally adjacent to the interrogated position of the position tag.

77. A method as defined in claim 75, further comprising:
displaying information describing the position of the projected image of the contact control area relative to the interrogated position of the position tag.

78. A method as defined in claim 77, further comprising:
covering the surgeon's face with a face shield during the surgical procedure; and
projecting on the face shield information describing the position of the contact control area on the floor relative to the interrogated position of the position tag.

79. A method as defined in claim 77, further comprising:
obtaining information from the surgical equipment concerning the status, control and functionality of the surgical equipment;
using patient monitoring equipment during the surgical procedure to determine information describing a condition of the patient;
obtaining the information from the patient monitoring equipment describing the condition of the patient; and
displaying the information describing the status, control and functionality of the surgical equipment and the information describing the condition of the patient on a display remote from the patient monitoring equipment.

80. A method as defined in claim 79, further comprising:
covering the surgeon's face with a face shield during the surgical procedure;
projecting on the face shield the information describing the position of the projected image of the contact control area relative to the interrogated position of the position tag, the information describing the status, control and functionality of the surgical equipment and the information describing the condition of the patient.

81. A method as defined in claim 74, further comprising:
indicating proximity of the position tag relative to the contact control area.

82. A method as defined in claim 63, further comprising:
associating an identification tag with at least one of the surgeon or the patient;
presenting information at the identification tag describing at least one of the surgeon, the patient or the surgical procedure to be performed on the patient;
reading the information from the identification tag; and
establishing an initial operative setting of the surgical equipment automatically in response to the information read from the identification tag.

83. A method as defined in claim 82, further comprising:
optically reading the information from the identification tag.

84. A method as defined in claim 82, further comprising:
presenting information at the identification tag describing the initial operative setting of the surgical equipment; and
establishing the initial operative setting of the surgical equipment automatically in response to reading the information describing the initial operative selling from the identification tag.

85. A method as defined in claim 82, further comprising:
presenting information at the identification tag which describes the surgeon;
storing information which describes the surgeon's preferred initial operative selling of the surgical equipment;
correlating the information which describes the surgeon with the stored information; and
establishing the initial operative selling of the surgical equipment based on correlating the information which describes the surgeon and the stored information.

86. A method as defined in claim 85, further comprising:
presenting information at the identification tag which describes the surgical procedure to be performed on the patient;
storing information which describes the surgeon's preferred initial operative settings of the surgical equipment for each of a plurality of different surgical procedures;
correlating the information which describes the surgical procedure with the stored information; and
establishing the initial operative selling of the surgical equipment based on correlating the described surgical procedure and the stored information.

87. A method as defined in claim 63, further comprising:
associating an identification tag with the surgeon;
presenting information at the identification tag describing the surgeon;

reading the information from the identification tag;
supplying override information from a source other than the identification tag; and
permitting operation of the surgical equipment only in response to the information which describes the surgeon read from the identification tag or in response to the override information supplied.

88. A method as defined in claim 87, further comprising: supplying a password as the override information.

89. A method as defined in claim 63, further comprising:
attaching an identification tag attached to the hand of the surgeon;
presenting information at the identification tag describing the surgeon;
reading the information from the identification tag;
interacting the hand of the surgeon with the image; and
permitting control of the surgical equipment only in response to the interaction of the hand of the surgeon to which the tag is attached with the image.

90. A method as defined in claim 63, further comprising:
projecting an optical image of the control device on the surface;
including a contact control area within the image which represents a control function of the surgical equipment;
creating a portion of the image separate from the contract control area;
obtaining information from the surgical equipment concerning the status, control and functionality of the surgical equipment; and
displaying the information describing the control, status and functionality of the surgical equipment in the portion of the image separate from the contact control area.

91. A method as defined in claim 63, further comprising:
using patient monitoring equipment attached to the patient during the surgical procedure to determine information describing a condition of the patient;
projecting an optical image of the control device on the surface;
including a contact control area within the image which represents a control function of the surgical equipment;
creating a portion of the image separate from the contract control area;
obtaining information from the patient monitoring equipment describing the condition of the patient; and
displaying the information describing the condition of the patient in the portion of the image separate from the contact control area.

92. A method as defined in claim 63, further comprising:
using patient monitoring equipment attached to the patient during the surgical procedure to determine information describing a condition of the patient;
projecting an optical image of the control device on the surface;
including a contact control area within the image which represents a control function of the surgical equipment;
creating a portion of the image separate from the contact control area;
obtaining information from the surgical equipment concerning the status, control and functionality of the surgical equipment;
obtaining information from the patient monitoring equipment describing the condition of the patient;
displaying the information describing the control, status and functionality of the surgical equipment; and
the information describing the condition of the patient in the portion of the image separate from the contact control area.

93. A method as defined in claim 92, further comprising:
optically interrogating one of the finger or foot of the surgeon with the contact control area of the image to control the surgical equipment.

94. A method of controlling surgical equipment in an operating room while a surgeon performs a surgical procedure on a patient, comprising:
associating an identification tag to at least one of the patient or the surgeon;
presenting information at the identification tag describing at least one of the surgeon, a hand of the surgeon, a foot of the surgeon, the patient or the surgical procedure to be performed on the patient;
presenting an image of a control device for the surgical equipment;
interrogating interaction of the surgeon with the control device image;
reading information from the identification tag while the surgeon interacts with the image; and
controlling the surgical equipment only in response to the interaction with the image by the surgeon who is described by the information or read from the identification tag.

95. A method as defined in claim 94, further comprising:
reading the information from the identification tag; and
establishing an initial operative setting of the surgical equipment automatically in response to the information read from the identification tag.

96. A method as defined in claim 95, further comprising:
presenting information at the identification tag which describes the surgeon;
storing information which describes the surgeon's preferred initial operative setting of the surgical equipment;
correlating the description of the surgeon obtained from reading the identification tag with the stored information; and
establishing the initial operative selling of the surgical equipment based on correlating the described surgeon and the stored information.

97. A method as defined in claim 96, further comprising:
presenting information at the identification tag which describes the surgical procedure to be performed on the patient;
storing information which describes the surgeon's preferred initial operative settings of the surgical equipment for each of a plurality of different surgical procedures;
correlating the described surgical procedure with the stored information; and
establishing the initial operative setting of the surgical equipment based on the correlation between the described surgical procedure and the stored information.

98. A method as defined in claim 94, further comprising:
optically reading the information from the identification tag.

99. A method as defined in claim 94, further comprising:
presenting information at the identification tag describing the initial operative setting of the surgical equipment; and establishing the initial operative setting of the surgical equipment automatically in response to the information describing the initial operative setting read from the identification tag.

100. A method as defined in claim 94, further comprising:
uttering voice commands; and
controlling the display image in response to the voice commands.

101. A method as defined in claim 94, further comprising:
associating the identification tag with the surgeon by the surgeon wearing the identification tag.

102. A method as defined in claim 101, further comprising:
the surgeon wearing the identification tag on at least one of a surgical gown, a surgical glove or a foot cover.

103. A method as defined in claim 94, further comprising:
associating the identification tag with the patient by attaching the identification tag to surgical drapes which cover the patient during the procedure.

104. A method as defined in claim 94, further comprising:
associating the identification tag with the patient by attaching the identification tag to the patient's body during the surgical procedure.

105. A method as defined in claim 94, further comprising:
presenting information at the one identification tag which describes the surgeon and the patient;
accessing information stored in memory which correlates the surgeon with the patient; and
permitting operation of the surgical equipment only in response to the information read from the one identification tag correlating the surgeon and the patient.

106. A method as defined in claim 94, further comprising:
presenting information at the one identification tag which describes the surgeon;
permitting operation of the surgical equipment only in response to information read from the one identification tag which describes the surgeon; and
permitting operation of the surgical equipment in response to override information if the information read from the one identification tag does not describe the surgeon.

107. A method as defined in claim 94, further comprising:
presenting information at the one identification tag which describes the surgeon;
the system controller accesses information stored in memory which correlates the surgeon with the surgeon's preferred initial operative setting of the surgical equipment; and
creating a display image presenting the information describing the surgeon's preferred initial operative setting of the surgical equipment.

108. A method as defined in claim 94, further comprising:
associating the identification tag with the surgeon by attaching the identification tag to the hand of the surgeon, the identification tag attached to the hand of the surgeon constituting a surgeon identification tag;
presenting information at the surgeon identification tag identifying the surgeon;
reading the information form the surgeon identification tag;
projecting a light image of the control device adjacent to a surgical site within a sterile field;
interacting with the control device image by using the hand of the surgeon; and
permitting control of the surgical equipment only in response to the interaction of the hand of the surgeon upon which the surgeon identification tag is attached with the control device image.

109. A method as defined in claim 94, further comprising:
associating an identification tag with each of the patient and the surgeon, the identification tag associated with the patient constituting a patient identification tag and the identification tag associated with the surgeon constituting a surgeon identification tag;
presenting information at the surgeon identification tag which describes at least one of the surgeon, the patient or the surgical procedure to be performed on the patient;
presenting information at the patient identification tag which describes at least one of the surgeon, the patient or the surgical procedure to be performed on the patient;
reading the information from the surgeon identification tag and the patient identification tag;
permitting operation of the surgical equipment in response to correlation of the information mad from the surgeon identification tag and the information read from the patient identification tag.

110. A method as defined in claim 94, further comprising:
associating the identification tag with the surgeon by attaching the identification tag to the foot of the surgeon, the identification tag attached to the foot of the surgeon constituting a surgeon identification tag;
presenting information at the surgeon identification tag describing the surgeon;
reading the information from the surgeon identification tag;
projecting a light image of the control device on the floor of the operating room;
interacting with the control device image by using the toot of the surgeon; and
permitting control of the surgical equipment only by interacting with the control device image with the toot of the surgeon upon which the surgeon identification tag is attached.

111. A method as defined in claim 110, further comprising:
including a control area within the control device image which represents an activation function of the surgical equipment; and
interacting the foot of the surgeon with the control area which represents the activation function.

112. A method as defined in claim 111, further comprising:
projecting the control device image on the floor at a position relative to the position of the surgeon identification tag.

* * * * *